(12) United States Patent
Shibata et al.

(10) Patent No.: US 9,649,621 B2
(45) Date of Patent: May 16, 2017

(54) METHOD OF FORMULATING ALKYLENE OXIDE CATALYST IN RELATION TO CATALYST REFERENCE PROPERTIES

(71) Applicant: Dow Technology Investments LLC, Midland, MI (US)

(72) Inventors: Hirokazu Shibata, Bergen op Zoom (NL); Arun G. Basrur, Pune (IN); Srikant Gopal, Yerwada Pune (IN); Mark H. McAdon, Midland, MI (US); Albert Cheng-Yu Liu, Charleston, WV (US); Liping Zhang, Lake Jackson, TX (US); Ernest R. Frank, Lake Jackson, TX (US)

(73) Assignee: Dow Technology Investments LLC, Midland, MI (US)

( * ) Notice: Subject to any disclaimer, the term of this patent is extended or adjusted under 35 U.S.C. 154(b) by 339 days.

(21) Appl. No.: 14/366,058

(22) PCT Filed: Nov. 30, 2012

(86) PCT No.: PCT/US2012/067200
§ 371 (c)(1),
(2) Date: Jun. 17, 2014

(87) PCT Pub. No.: WO2013/095888
PCT Pub. Date: Jun. 27, 2013

(65) Prior Publication Data
US 2014/0323295 A1 Oct. 30, 2014

Related U.S. Application Data

(60) Provisional application No. 61/577,219, filed on Dec. 19, 2011.

(51) Int. Cl.
*B01J 23/48* (2006.01)
*B01J 23/68* (2006.01)
(Continued)

(52) U.S. Cl.
CPC .............. *B01J 23/688* (2013.01); *B01J 23/66* (2013.01); *B01J 27/055* (2013.01); *B01J 35/023* (2013.01);
(Continued)

(58) Field of Classification Search
CPC ...... B01J 23/688; B01J 37/0036; B01J 23/66; B01J 27/055; B01J 35/023; B01J 35/1009;
(Continued)

(56) References Cited

U.S. PATENT DOCUMENTS 3,962,136 A  6/1976 Nielsen et al.
4,012,425 A  3/1977 Nielsen et al.
(Continued)

FOREIGN PATENT DOCUMENTS

EP  0266015 A1  10/1987
EP  0352850 B1  1/1989
(Continued)

OTHER PUBLICATIONS

Written Opinion of the International Preliminary Examining Authority (IPEA) dated, Nov. 25, 2013.
(Continued)

*Primary Examiner* — Colleen Dunn
*Assistant Examiner* — Haytham Soliman
(74) *Attorney, Agent, or Firm* — Hansen IP Law PLLC

(57) ABSTRACT

Methods of preparing a second high-efficiency, rhenium-promoted silver catalyst for producing alkylene oxide from an alkylene based on a first catalyst are disclosed and described. In accordance with the disclosed methods, the first and second catalysts include at least one promoter that includes a rhenium promoter. The target catalyst concentrations of one or more promoters of the at least one promoter on the second catalyst are determined based on the values of (Continued)

a catalyst reference property for the two catalysts and the concentration of the one or more promoters of the at least one promoter on the first catalyst. Suitable catalyst reference properties include carrier specific surface area and silver specific surface area. Reaction systems utilizing the first and second catalysts are also described.

10 Claims, 5 Drawing Sheets

(51) Int. Cl.
*B01J 37/02* (2006.01)
*B01J 35/10* (2006.01)
*C07D 301/10* (2006.01)
*B01J 23/66* (2006.01)
*B01J 27/055* (2006.01)
*B01J 35/02* (2006.01)
*B01J 37/00* (2006.01)

(52) U.S. Cl.
CPC ....... *B01J 35/1009* (2013.01); *B01J 35/1042* (2013.01); *B01J 37/0036* (2013.01); *B01J 37/0205* (2013.01); *B01J 37/0207* (2013.01); *B01J 37/0213* (2013.01); *C07D 301/10* (2013.01); *Y02P 20/582* (2015.11)

(58) Field of Classification Search
CPC B01J 35/1042; B01J 37/0207; B01J 37/0205; B01J 37/0213; C07D 301/10; Y02P 20/582
USPC .............. 502/348, 220, 219, 216, 324, 347; 549/534
See application file for complete search history.

(56) References Cited

U.S. PATENT DOCUMENTS

| | | |
|---|---|---|
| 4,761,394 A | 8/1988 | Lauritzen |
| 4,810,689 A | 3/1989 | Hayden |
| 5,145,824 A | 9/1992 | Buffum et al. |
| 5,380,697 A | 1/1995 | Matusz et al. |
| 5,387,751 A | 2/1995 | Hayden et al. |
| 5,504,053 A | 4/1996 | Chou et al. |
| 5,733,842 A | 3/1998 | Gerdes et al. |
| 2009/0177000 A1 | 7/2009 | Natal et al. |
| 2010/0280261 A1 | 11/2010 | Howard et al. |
| 2014/0088316 A1 | 3/2014 | Natal et al. |
| 2014/0100379 A1 | 4/2014 | Richard et al. |

FOREIGN PATENT DOCUMENTS

| | | |
|---|---|---|
| EP | 0425020 B1 | 10/1990 |
| EP | 0266015 B1 | 12/1991 |
| EP | 0789693 B1 | 10/1995 |
| EP | 1613428 B1 | 10/2007 |
| WO | 9613493 A1 | 5/1996 |
| WO | 03072246 A2 | 9/2003 |
| WO | 03072246 A3 | 9/2003 |
| WO | 2004089537 A3 | 10/2004 |
| WO | 2007123932 A2 | 11/2007 |
| WO | 2013055716 A1 | 4/2013 |

OTHER PUBLICATIONS

Response as-Filed to the Written Opinion of the International Preliminary Examining Authority (IPEA) dated, Jan. 22, 2014.
International Search Report and Written Opinion dated, Apr. 11, 2013.
Response as-filed to the International Search Report and Written Opinion dated, Oct. 17, 2013.
International Preliminary Report on Patentability (IPRP) dated, Apr. 7, 2014.
Boudart, M., Turnover Rates in Heterogeneous Catalysis; Chemical Reviews, vol. 95, No. 3, pp. 661-666 (1995).

METHOD OF FORMULATING ALKYLENE OXIDE CATALYST IN RELATION TO CATALYST REFERENCE PROPERTIES

TECHNICAL FIELD

This disclosure relates generally to high-efficiency catalysts for making alkylene oxides, and more specifically, to a method of determining target catalyst promoter concentrations based on catalyst properties.

BACKGROUND

The production of alkylene oxides via catalytic epoxidation of olefins in the presence of oxygen using silver based catalysts is known. Conventional silver-based catalysts used in such processes typically provide a relatively lower efficiency or "selectivity" (i.e., a lower percentage of the reacted alkylene is converted to the desired alkylene oxide). In certain exemplary processes, when using conventional catalysts in the epoxidation of ethylene, the theoretically maximal efficiency towards ethylene oxide, expressed as a fraction of the ethylene converted, does not reach values above the 6/7 or 85.7 percent limit. Therefore, this limit had long been considered to be the theoretically maximal efficiency of this reaction, based on the stoichiometry of the following reaction equation:

$$7C_2H_4 + 6O_2 \rightarrow 6C_2H_4O + 2CO_2 + 2H_2O$$

cf. Kirk-Othmer's Encyclopedia of Chemical Technology, 4th ed., Vol. No. 9, 1994, p. 926.

Alkylene oxide catalysts comprise three main chemical components: silver, a carrier, and solid promoter packages. Certain "high efficiency" or "high selectivity" modern silver-based catalysts are highly selective towards alkylene oxide production. For example, when using certain modern catalysts in the epoxidation of ethylene, the theoretically maximal efficiency towards ethylene oxide can reach values above the 6/7 or 85.7 percent limit referred to, for example 88 percent or 89 percent, or above. As used herein, the terms "high efficiency catalyst" and "high selectivity catalyst" refer to a catalyst that is capable of producing an alkylene oxide from the corresponding alkylene and oxygen at an efficiency greater than 85.7 percent. The observed actual efficiency of a high efficiency catalyst may fall below 85.7 percent under certain conditions based on process variables, catalyst age, etc. However, if the catalyst is capable of achieving at least an 85.7 percent efficiency, it is considered to be a high efficiency catalyst. Such highly efficient catalysts, which may comprise as their active components silver, rhenium, at least one further metal, and optionally, a rhenium co-promoter, are disclosed in EP0352850B1 and in several subsequent patent publications. "Promoters," sometimes referred to as "inhibitors" or "moderators," refer to materials that enhance the performance of the catalysts by either increasing the rate towards the desired formation of alkylene oxide and/or suppressing the undesirable oxidation of olefin or alkylene oxide to carbon dioxide and water, relative to the desired formation of alkylene oxide. As used herein, the term "co-promoter" refers to a material that—when combined with a promoter—increases the promoting effect of the promoter. In addition, promoters may also be referred to as "dopants." In the case of those promoters that provide high efficiencies, the terms "high efficiency dopants" or "high selectivity dopants" may be used.

"Promoters" can be materials that are introduced to catalysts during the preparation of the catalysts (solid phase promoters, also referred to as "catalyst promoters" herein). In addition, "promoters" can also be gaseous materials that are introduced to the epoxidation reactor feed (gas phase promoters). In one example, an organic halide gas phase promoter may be added continuously to the epoxidation reactor feed to increase the catalyst efficiency. For silver-based ethylene epoxidation catalysts, both solid and gas phase promoters are typically required in any commercial processes.

Conventional catalysts have relatively flat efficiency curves with respect to the gas phase promoter concentration in the feed, i.e., the efficiency is almost invariant (i.e., the change in efficiency with respect to a change in gas phase promoter concentration in the feed is less than about 0.1%/ppm) over a wide range of promoter concentrations, and this invariance is substantially unaltered as reaction temperature is changed (i.e., the change in efficiency with respect to a change in reaction temperature is less than about 0.1%/° C.) during prolonged operation of the catalyst. However, conventional catalysts have nearly linear activity decline curves with respect to the gas phase promoter concentration in the feed, i.e., with increasing gas phase promoter concentration in the feed, temperature has to be increased or the alkylene oxide production rate will be reduced. Therefore, when using a conventional catalyst, for optimum efficiency, the gas phase promoter concentration in the feed can be chosen at a level at which the maximum efficiency can be maintained at relatively lower operating temperatures. Typically, the gas phase promoter concentration can remain substantially the same during the entire lifetime of a conventional catalyst. Alternatively, the reaction temperature may be adjusted to obtain a desired production rate without any substantial impact on efficiency.

By contrast, high efficiency catalysts tend to exhibit relatively steep efficiency curves as a function of gas phase promoter concentration as the concentration moves away from the value that provides the highest efficiency (i.e., the change in efficiency with respect to a change in gas phase promoter concentration is at least about 0.2%/ppm when operating away from the efficiency maximizing concentration). Thus, small changes in the promoter concentration can result in significant efficiency changes, and the efficiency exhibits a pronounced maximum, i.e., an optimum, at certain concentrations (or feed rates) of the gas phase promoter for a given reaction temperature and catalyst age as well as other conditions such as feed gas composition. Moreover, the efficiency curves and the optimum gas phase promoter concentration tend to be strong functions of reaction temperature and are thus significantly affected if reaction temperature is varied, for example, to compensate for decreases in catalyst activity, (i.e., the change in efficiency with respect to a change in reaction temperature can be at least about 0.1%/° C. when operating away from the efficiency maximizing promoter concentrations for the selected temperatures). In addition, high efficiency catalysts have exhibited significant activity increases with increases in the gas phase promoter concentration in the feed, i.e., with increasing gas phase promoter concentration in the feed, temperature has to be decreased or the production rate will increase.

Variations in high-efficiency catalyst properties can yield undesirable variations in catalyst activities, which in turn, can result in different catalyst operating temperatures. Variations in catalyst operating temperatures can result in the need to use different gas-phase promoter concentrations and different optimum values for such concentrations. Optimum process conditions developed for catalysts having particular physical or chemical property values may be sub-optimum for catalysts having different values for such properties.

It is typical for high-efficiency alkylene oxide catalysts to exhibit variability of physical properties, such as carrier specific surface area, silver specific surface area, carrier porosity, carrier total pore volume, and shape even when all manufacturing process parameters are well-controlled. This variability is attributable, at least in part, to natural variations in the raw materials used to prepare the carrier and the inherent variability of the carrier manufacture process. If such variations are not handled properly, it may result in variable and less predictable alkylene oxide catalyst properties and performance.

The physical properties of high-efficiency alkylene oxide catalysts, such as the carrier specific surface area (e.g., surface area/carrier mass) may vary from batch to batch of catalyst, resulting in variable and less predictable process performance. The inconsistency of catalyst performance may result in difficulty in running reaction systems comprising multiple catalyst batches. It particular, such inconsistencies can result in less stable operation, lower selectivity, and shortened catalyst life cycle. It is typical for a multi-reactor system to share a common feed gas mixture. When the catalyst activity varies significantly among different reactors and/or among the tubes within the same reactor, it could lead to hot spots or runaway reactions in catalyst regions of relatively high catalyst activity. For high efficiency alkylene oxide catalysts in particular, catalyst activity and efficiency both heavily depend on the level of the gas phase promoters. The optimum levels of such gas-phase promoters are in turn strongly dependent on reaction temperature. Thus, a higher variation in catalyst intrinsic activity may lead to problems with reactor temperature control and/or continued sub-optimized operation. The consequences could be loss of both short-term and long-term catalyst performance.

Certain references have disclosed multiple catalyst formulations in which the catalyst concentration of a particular promoter varies with the carrier specific surface area. Other references have characterized promoter concentrations based on their ratios to carrier specific surface area. However, such references have not acknowledged the advantages of or suggested adjusting promoter concentrations based on catalyst properties—such as catalyst physical properties like carrier specific surface area and silver specific surface area—when formulating a high-efficiency alkylene oxide catalyst to achieve consistent predictable performance. Nor do such references teach how to make different catalyst batches having substantially uniform performance properties when the carrier properties such as carrier specific surface areas are significantly different. Nor have such references distinguished between promoters whose concentrations can beneficially be scaled based on catalyst carrier specific surface area and those that cannot. In addition, they have failed to acknowledge or appreciate the advantages of scaling the concentrations of particular promoters, such as cesium, rhenium, sodium, lithium and/or sulfur or sulfate, with respect to any catalyst physical properties, including carrier specific surface area. Thus, a need has arisen for a catalyst preparation method and reaction system that achieves catalyst performance expectations, maintains predictable low risk operating characteristics with respect to temperature, gas phase promoter levels, and aging, and/or which provides the ability to beneficially utilize catalyst carrier lots with varying carrier specifications (e.g., carrier specific surface area). In addition, it is desirable to accelerate catalyst manufacturing timelines by using prior catalyst data in situations where extensive lab-scale testing for the purpose of optimizing solid-phase promoter levels is not available prior to catalyst production.

SUMMARY

A method for making a second high efficiency, alkylene oxide catalyst based on the properties of a first high efficiency alkylene oxide catalyst is provided. The first high efficiency alkylene oxide catalyst comprises a carrier, silver, and a promoting amount of at least one promoter, the at least one promoter comprising a rhenium promoter. The method comprises determining a respective target concentration value on the second catalyst for one or more of the at least one promoter based on values of a catalyst reference property for the first and second catalysts and a respective concentration value of the one or more of the at least one promoter on the first catalyst. The method also comprises preparing the second high efficiency catalyst based on the respective target concentration value on the second catalyst for the one or more of the at least one promoter.

A reaction system for producing alkylene oxide from a feed gas comprising an alkylene and oxygen is also provided. The reaction system comprises at least a first high-efficiency alkylene oxide catalyst and a second high-efficiency alkylene oxide catalyst. The first catalyst comprises silver, a carrier, and a promoting amount of at least one promoter, the at least one promoter comprising a rhenium promoter. The second catalyst comprises silver, a carrier, and a promoting amount of at least one promoter. The at least one promoter comprises a rhenium promoter, such that the respective ratios between the respective concentrations of one or more promoters of the at least one promoter on the second catalyst and the respective concentrations of the one or more promoters on the first catalyst are respective functions of a catalyst reference property.

DETAILED DESCRIPTION

Figure 1A:
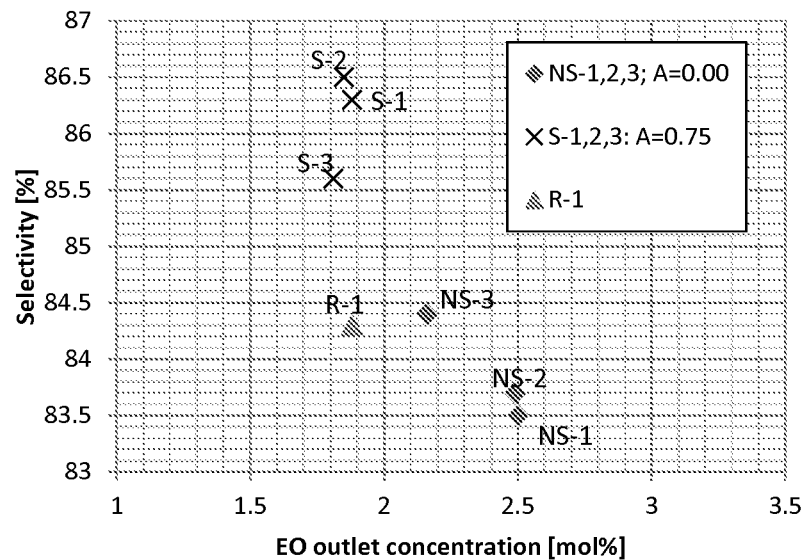
FIG. 1A is a graph of the maximized efficiency toward the production of ethylene oxide versus the corresponding reactor outlet ethylene oxide concentration in a process for making ethylene oxide from ethylene and oxygen using a variety of high-efficiency ethylene oxide catalysts with different promoter scaling multipliers at a reaction temperature of 231° C.

As discussed below, the present disclosure provides a method for determining target concentration values of the catalyst concentrations of some or all of the solid promoters in certain high-efficiency alkylene oxide catalysts based on a catalyst reference property, such as a physical property of the catalyst. In certain examples, the physical property on which the determination is based is the carrier specific surface area (carrier area/carrier mass). In other examples, the physical property is the specific surface area of the primary catalytic material (silver). In further examples, the target concentration values of certain promoters are determined based on the catalyst carrier specific surface area, and the target concentrations of certain other promoters are determined based on the primary catalytic material specific surface area.

In order to facilitate an understanding of the present disclosure, it is useful to define certain terms relating to catalyst and process performance. The activity of a catalyst in a fixed bed reactor is generally defined as the reaction rate towards the desired product per unit of catalyst volume in the reactor. The activity relates to both the total number of available active sites and the reaction rate of each site. The number of active sites can be reduced in several ways. For example, they can be reduced by coalescence of the silver particles, which reduces the surface area of the silver available for reaction. They can also be reduced by poisoning, for example by reaction with trace sulfur compounds in the reactor feed. The number of active sites can also be reduced by reaction with normal process constituents, such as by reaction with chloride compounds in the process stream to form silver chloride compounds, such as bulk type AgCl, which are inactive towards the epoxidation reaction. The activity will also decline if the reaction rate goes down for at least some of the active sites (e.g., due to localized poisoning) independent of the total number of active sites. To compensate for the activity decline in order to maintain a given production rate, certain reaction conditions have to be changed to increase the overall production rate of the available active sites. For instance, reaction temperature is often raised to provide more energy to the active sites for this purpose. "Activity" can be quantified in a number of ways, one being the mole percent of alkylene oxide contained in the outlet stream of the reactor relative to that in the inlet stream (the mole percent of alkylene oxide in the inlet stream typically, but not necessarily, approaches zero percent) while the reaction temperature is maintained substantially constant; and another being the temperature required to maintain a given rate of alkylene oxide production. In many instances, activity is measured over a period of time in terms of the mole percent of alkylene oxide produced at a specified constant temperature. Alternatively, activity may be measured as a function of the temperature required to sustain production of a specified constant mole percent of alkylene oxide, such as ethylene oxide, given other conditions such as pressure and total moles in the feed.

The "efficiency" of the epoxidation, which is synonymous with "selectivity," refers to the relative amount (as a fraction or in percent) of converted or reacted olefin that forms a particular product. For example, the "efficiency to alkylene oxide" refers to the percentage on a molar basis of converted or reacted olefin that forms alkylene oxide. The "yield" of alkylene oxide refers to the net number of moles of alkylene oxide produced by the process divided by the net number of moles of olefin fed to the process for any given time period.

As used herein, the term "reaction product" includes unreacted feed components as well as those that are generated as a result of a chemical reaction. In the example of ethylene oxide processes, the "reaction product" would include ethylene oxide, and if present, any by-products (such as carbon dioxide) and/or unreacted feed components (such as ethylene, oxygen, and/or chlorides).

The catalysts described herein are used in processes for making an alkylene oxide from an alkylene and oxygen. The process generally uses a reactor comprising a tubular vessel with a catalyst bed disposed in it. An olefin (i.e., alkylene) feed stream (which may also include saturated hydrocarbons, such as ethane, as an impurity) is combined with a ballast gas, oxygen feed, and a gas phase promoter feed to define the reactor feed gas inlet stream proximate the reactor inlet. The reactor outlet stream includes the alkylene oxide ("AO") product, plus side products (e.g., $CO_2$, $H_2O$, and small amounts of saturated hydrocarbons), unreacted olefin, gas-phase promoters, oxygen, and inerts. An absorber with a water absorption medium absorbs alkylene oxide product from the reactor product stream, and the alkylene oxide is subsequently separated from the water. A recycle stream may also be provided to minimize waste and increase savings as the recycling of unreacted reactants decreases the amount of fresh "make up" feed (e.g., fresh alkylene, oxygen, and ballast gas) supplied to the reactor. Carbon dioxide may be removed from the recycle stream in a $CO_2$ removal unit (e.g., a $CO_2$ scrubber) to control the feed gas $CO_2$ concentration. A purge line may also be provided for the removal of saturated hydrocarbon impurities (e.g., ethane), inerts (such as argon and nitrogen), and/or byproducts (as well as carbon dioxide) to prevent their accumulation in the reactor feed.

The olefin comprising the olefin feed stream may be any olefin, including aromatic olefins and di-olefins, whether conjugated or not. However, preferred olefins are mono-olefins having the following formula:

wherein, $R_1$ and $R_2$ are individually selected from the group consisting of hydrogen and alkyl radicals having from 1 to 6 carbon atoms. Propylene ($R_1=CH_3$, $R_2=H$) and ethylene ($R_1=R_2=H$) are more preferred, and ethylene is most preferred. Correspondingly, preferred alkylene oxides in the reactor product stream are of the formula:

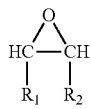

wherein, $R_1$ and $R_2$ are individually selected from the group consisting of hydrogen and alkyl radicals having from 1 to 6 carbon atoms. Propylene oxide ($R_1=CH_3$, $R_2=H$) and ethylene oxide ($R_1=R_2=H$) are more preferred, and ethylene oxide is most preferred.

The alkylene oxide reactor includes a high efficiency, silver catalyst. Generally, the highly efficient silver based catalyst is a supported catalyst. The support (also known as a "carrier") may be selected from a wide range of inert support materials. Such support materials may be natural or artificial inorganic materials and they include silicon carbide, clays, pumice, zeolites, charcoal and alkaline earth metal carbonates, such as calcium carbonate. Preferred are refractory support materials, such as alumina, magnesia, zirconia and silica. The most preferred support material is alpha alumina. In one exemplary embodiment, silver is deposited on the catalyst carrier as are one or more solid promoters, which are discussed further below.

There are many well-known methods of preparing supports suitable for use in ethylene oxide catalysts. Some of such methods are described in, for example, U.S. Pat. Nos. 4,379,134; 4,806,518; 5,063,195; 5,384,302, U.S. Patent Application 20030162655 and the like. For example, an alpha-alumina support of at least 95% purity can be prepared by compounding (mixing) the raw materials, extrusion, drying and a high temperature calcination. In this case, the starting raw materials usually include one or more alpha-alumina powder(s) with different properties, a clay-type material which may be added as binder to provide physical strength, and a burnout material (usually an organic compound) used in the mix to provide desired porosity after its removal during the calcination step. The levels of impurities in the finished carrier are determined by the purity of the raw materials used, and their degree of volatilization during the calcination step. Common impurities may include silica, alkali and alkaline earth metal oxides and trace amounts of metal and/or non-metal-containing additives. Another method for preparing a carrier having particularly suitable properties for ethylene oxide catalyst usage comprises optionally mixing zirconium silicate with boehmite alumina (AlOOH) and/or gamma-alumina, peptizing the aluminas with a mixture containing an acidic component and halide anions (preferably fluoride anions) to provide peptized halogenated alumina, forming (for example, by extruding or pressing) the peptized halogenated alumina to provide formed peptized halogenated alumina, drying the formed peptized halogenated alumina to provide dried formed alumina, and calcining the dried formed alumina to provide pills of optionally modified alpha-alumina carrier.

There have been employed alumina which has a very high purity, that is, at least 98 wt. % alpha-alumina, any remaining components being silica, alkali metal oxides (for example, sodium oxide) and trace amounts of other metal-containing and/or non-metal-containing additives or impurities. Likewise, there have been employed alumina of lower purity, that is, 80 wt. % alpha-alumina, the balance being one or more of amorphous and/or crystalline alumina and other alumina oxides, silica, silica alumina, mullite, various alkali metal oxides (for example, potassium oxide and cesium oxide), alkaline earth metal oxides, transition metal oxides (for example, iron oxide and titanium oxide), and other metal and non-metal oxides. In addition, the material used to make the carrier may comprise compounds which have been known for improving catalyst performance, for example, rhenium, (such as rhenates) and molybdenum.

In an especially preferred embodiment, the support material comprises at least 80 weight percent alpha alumina and less than 30 parts per million acid-leachable alkali metals by weight, the weight percent of the alpha alumina and the concentration of the acid-leachable alkali metals being calculated on the weight of the carrier, where the acid-leachable alkali metals are selected from lithium, sodium, potassium, and mixtures thereof.

The alpha alumina carrier prepared as described hereinabove preferably has a specific surface area of at least 0.5 $m^2/g$, and more preferably, at least 0.7 $m^2/g$. The surface area is typically less than 10 $m^2/g$, and preferably, less than 5 $m^2/g$. In a preferred embodiment of the methods and reaction systems described herein, the specific surface area corresponding to at least two of the different batches of the carrier used to prepare different batches of the epoxidation catalyst differ by at least 5%, preferably by at least 10%, or even more preferably by at least 20% or more based on the lower of the carrier specific surface areas. In other preferred embodiments, the ratios of the carrier specific surface areas of different batches of carrier used to prepare different batches of the epoxidation catalyst are at least 0.2, preferably at least 0.3, and more preferably at least 0.5. At the same time, the ratios of the carrier specific surface areas of different batches of carrier used to prepare different batches of the epoxidation catalyst are no more than 5, preferably no more than 3, and more preferably no more than 2. "Carrier specific surface area", as used herein, refers to the surface area per gram of carrier as measured by the BET (Brunauer, Emmett and Teller) method by nitrogen as described in the Journal of the American Chemical Society 60 (1938) pp. 309-316.

The alpha-alumina carrier preferably has a pore volume of at least 0.3 $cm^3/g$, and more preferably, from 0.4 $cm^3/g$ to 1.0 $cm^3/g$ and a median pore diameter from 1 to 50 microns. A variety of carrier morphologies may be used, including pills, cylinders, cylinders with one or more longitudinal axial openings, chunks, tablets, pieces, pellets, rings, spheres, wagon wheels, saddle rings and toroids having star shaped inner and/or outer surfaces. In a preferred embodiment, the high-purity alpha-alumina preferably includes particles many of which have at least one substantially flat major surface, and having a lamellate or platelet morphology. In a more preferred embodiment the particles approximate the shape of a hexagonal plate (some particles having two or more flat surfaces), at least 50 percent of which (by number) have a major dimension of less than 50 microns. In a preferred embodiment, the alpha-alumina carrier comprises zirconium silicate (zircon), present substantially as zirconium silicate in the finished carrier, more preferably, in an amount up to 4 weight percent, calculated on the weight of the carrier.

The catalysts described herein for producing alkylene oxide, for example, ethylene oxide or propylene oxide, may be prepared with the aforementioned carriers by impregnating the carrier with a solution of one or more silver compounds, depositing the silver throughout the pores of the carrier and reducing the silver compound as is well known in the art. See for example, Liu, et al., U.S. Pat. No. 6,511,938 and Thorsteinson et al., U.S. Pat. No. 5,187,140.

Generally, the carrier is impregnated with a catalytic amount of silver, which is any amount of silver capable of catalyzing the direct oxidation of the alkylene with oxygen or an oxygen-containing gas to the corresponding alkylene oxide. In making such a catalyst, the carrier is typically impregnated (one or more times) with one or more silver compound solutions sufficient to allow the silver to be supported on the carrier in an amount greater than 5 percent, preferably greater than 10 percent, more preferably greater than 15 percent, more preferably greater than 20 percent, yet more preferably greater than 25 percent, still more preferably, greater than 27 percent, and even more preferably, greater than 30 percent by weight, based on the weight of the catalyst. Typically, the amount of silver supported on the carrier is less than 70 percent, and more preferably, less than 50 percent by weight, based on the weight of the catalyst.

Although silver particle size in the finished catalyst is important, the range is not narrow. A suitable silver particle size can be in the range of from 10 to 10,000 angstroms in diameter. A preferred silver particle size ranges from greater than 100 to less than 5,000 angstroms in diameter. It is desirable that the silver be relatively uniformly dispersed within, throughout, and/or on the alumina carrier.

As is known to those skilled in the art, there are a variety of known promoters, that is, materials which, when present in combination with particular catalytic materials, for example, silver, benefit one or more aspect of catalyst performance or otherwise act to promote the catalyst's ability to make a desired product, for example ethylene oxide or propylene oxide. Such promoters in themselves are generally not considered catalytic materials. The presence of such promoters in the catalyst has been shown to contribute to one or more beneficial effects on the catalyst performance, for example enhancing the rate or amount of production of desired product, reducing the temperature required to achieve a suitable rate of reaction, reducing the rates or amounts of undesired reactions, etc. Competing reactions occur simultaneously in the reactor, and a critical factor in determining the effectiveness of the overall process is the measure of control one has over these competing reactions. A material which is termed a promoter of a desired reaction can be an inhibitor of another reaction, for example a combustion reaction. What is significant is that the effect of the promoter on the overall reaction is favorable to the efficient production of the desired product, for example ethylene oxide. The concentration of the one or more promoters present in the catalyst may vary over a wide range depending on the desired effect on catalyst performance, the other components of a particular catalyst, the physical and chemical characteristics of the carrier, and the epoxidation reaction conditions.

There are at least two types of promoters: solid-phase promoters and gaseous promoters. The solid-phase and/or gaseous promoters are provided in a promoting amount. A "promoting amount" of a certain component of a catalyst refers to an amount of that component that works effectively to provide an improvement in one or more of the catalytic properties of that catalyst when compared to a catalyst not containing said component. Examples of catalytic properties include, inter alia, operability (e.g., resistance to run-away), efficiency, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced efficiency at one set of operating conditions may be operated at a different set of conditions wherein the improvement shows up in the activity rather than the efficiency, and an operator of an ethylene oxide plant will intentionally change the operating conditions in order to take advantage of certain catalytic properties even at the expense of other catalytic properties in order to maximize profits by taking into account feedstock costs, energy costs, by-product removal costs, turnaround schedules, and the like.

The promoting effect provided by the promoters can be affected by a number of variables such as for example, reaction conditions, catalyst preparative techniques, carrier specific surface area, pore structure, and surface chemical properties of the carrier such as carrier acidity, the silver and co-promoter content of the catalyst, the silver specific area of the catalyst, the presence of other cations and anions present on the catalyst. The presence of other activators, stabilizers, promoters, enhancers or other catalyst improvers can also affect the promoting effects. The optimum promoter concentrations depend on the desired catalyst performance targets, e.g., catalyst life, efficiency, workrate, etc. They are also affected by plant-specific process conditions such as reactor system design, temperature limits, pressure, GHSV, and reactor inlet and outlet gas stream compositions. For example, the reactor inlet gas $CO_2$ concentration and desired catalyst workrate can largely determine the optimum promoter levels because catalyst activity and efficiency will need to be balanced. They may also depend on the catalyst and carrier physical properties and composition, such as silver content and the amounts of other promoters.

In certain examples, the high-efficiency alkylene oxide catalyst solid-phase promoters include at least one solid-phase scaled promoter. The term "scaled promoter" refers to a promoter having a target catalyst concentration that is scaled based on a reference property of the catalyst, such as carrier specific surface area and/or silver specific surface area. Conversely, the term "non-scaled promoter" refers to a promoter that is not a scaled promoter.

Examples of well-known solid-phase promoters for catalysts used to produce ethylene oxide include compounds of lithium, sodium, potassium, rubidium, cesium, rhenium, sulfur, manganese, molybdenum, and tungsten. During the reaction to make ethylene oxide, the specific form of the promoter on the catalyst may be unknown. Examples of solid-phase promoter compositions and their characteristics as well as methods for incorporating the promoters as part of the catalyst are described in Thorsteinson et al., U.S. Pat. No. 5,187,140, particularly at columns 11 through 15, Liu, et al., U.S. Pat. No. 6,511,938, Chou et al., U.S. Pat. No. 5,504,053, Soo, et al., U.S. Pat. No. 5,102,848, Bhasin, et al., U.S. Pat. Nos. 4,916,243, 4,908,343, and 5,059,481, and Lauritzen, U.S. Pat. Nos. 4,761,394, 4,766,105, 4,808,738, 4,820,675, and 4,833,261. The solid-phase promoters are generally added as chemical compounds to the catalyst prior to its use. As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions when added as a compound to the catalyst. Once in the catalyst, the form of the promoter is not always known, and the promoter may be present without the counterion added during the preparation of the catalyst. For example, a catalyst made with cesium hydroxide may be analyzed to contain cesium but not hydroxide in the finished catalyst. Likewise, compounds such as alkali metal oxide, for example cesium oxide, or transition metal oxides, for example $MoO_3$, while not being ionic, may convert to ionic compounds during catalyst preparation or in use. For the sake of ease of understanding, the solid-phase promoters will be referred to in terms of cations and anions regardless of their form in the catalyst under reaction conditions.

The catalyst prepared on the carrier may contain alkali metal and/or alkaline earth metal as cation promoters. Exemplary of the alkali metal and/or alkaline earth metals are lithium, sodium, potassium, rubidium, cesium, beryllium, magnesium, calcium, strontium and barium. Other cation promoters include Group 3b metal ions including lanthanide series metals. In some instances, the promoter comprises a mixture of cations, for example cesium and at least one other alkali metal, to obtain a synergistic efficiency enhancement as described in U.S. Pat. No. 4,916,243. Note that references to the Periodic Table herein shall be to that as published by the Chemical Rubber Company, Cleveland, Ohio, in CRC Handbook of Chemistry and Physics, 46th Edition, inside back cover.

The concentration of the alkali metal promoters in the finished catalyst is not narrow and may vary over a wide range. The optimum alkali metal promoter concentration for a particular catalyst will be dependent upon performance characteristics, such as catalyst efficiency, rate of catalyst aging and reaction temperature. In addition, in preferred examples, the alkali metal promoter concentrations should be adjusted according to the content of oxyanion promoters so that one balances the other. In accordance with the catalyst preparation methods and reaction systems disclosed herein, the optimum alkali metal promoter concentration for a particular catalyst may also depend on a reference property of the catalyst, including catalyst physical properties, examples of which include carrier specific surface area and silver specific surface area.

The concentration of alkali metal (based on the weight of cation, for example cesium) in the finished catalyst may vary from 0.0005 to 1.0 wt. %, preferably from 0.005 to 0.5 wt. %. The preferred amount of cation promoter deposited on or present on the surface of the carrier or catalyst generally lies between 10 and 4000, preferably 15 and 3000, and more preferably between 20 and 2500 ppm by weight of cation calculated on the total carrier material. Cation promoter amounts between 50 and 2000 ppm by weight of the total carrier material are frequently most preferable. When the alkali metal cesium cation is used in mixture with other cations, the ratio of cesium to any other alkali metal and alkaline earth metal cation(s), if used, to achieve desired performance is not narrow and may vary over a wide range. The weight ratio of cesium to the other cation promoters may vary from 0.0001:1 to 10,000:1, preferably from 0.001:1 to 1,000:1.

Examples of some of the anion promoters which may be employed with the present invention include the halides, for example fluorides and chlorides, and the oxyanions of the elements other than oxygen having an atomic number of 5 to 83 of Groups 3b to 7b and 3a to 7a of the Periodic Table. One or more of the oxyanions of nitrogen, sulfur, manganese, tantalum, molybdenum, tungsten and rhenium may be preferred for some applications.

The types of anion promoters or modifiers suitable for use in the catalysts of this invention comprise, by way of example only, oxyanions such as sulfate, $[SO_4]^{-2}$, phosphates, for example, $[PO_4]^{-3}$, titanates, e g., $[TiO_3]^{-2}$, tantalates, for example, $[Ta_2O_6]^{-2}$, molybdates, for example, $[MoO_4]^{-2}$, vanadates, for example, $[V_2O_4]^{-2}$, chromates, for example, $[CrO_4]^{-2}$, zirconates, for example, $[ZrO_3]^{-2}$, polyphosphates, manganates, nitrates, chlorates, bromates, borates, silicates, carbonates, tungstates, thiosulfates, cerates, rhenates, perrhenates, niobates, and the like. The halides may also be present, including fluoride, chloride, bromide and iodide.

It is well recognized that many anions have complex chemistries and may exist in one or more forms, for example, orthovanadate and metavanadate; and the various molybdate oxyanions such as $[MoO_4]^{-2}$, and $[Mo_7O_{24}]^{-6}$ and $[Mo_2O_7]^{-2}$. The oxyanions may also include mixed metal-containing oxyanions including polyoxyanion structures. For instance, manganese and molybdenum can form a mixed metal oxyanion. Similarly, other metals, whether provided in anionic, cationic, elemental or covalent form may enter into anionic structures.

While an oxyanion, or a precursor to an oxyanion, may be used in solutions impregnating a carrier, it is possible that during the conditions of preparation of the catalyst and/or during use, the particular oxyanion or precursor initially present may be converted to another form. Indeed, the element may be converted to a cationic or covalent form. In many instances, analytical techniques may not be sufficient to precisely identify the species present. The invention is not intended to be limited by the exact species that may ultimately exist on the catalyst during use.

The highly efficient catalysts described herein, comprise rhenium, which can be provided in various forms, for example, as the metal, as a covalent compound, as a cation or as an anion. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, ammonium perrhenate, alkaline earth metal perrhenates, silver perrhenates, other perrhenates and rhenium heptoxide can also be suitably utilized. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, that is, $[ReO_4]^{-1}$. Similar chemistries can be exhibited by other metals such as molybdenum and tungsten.

Another class of promoters, which may be employed with the present invention, includes manganese components. In many instances, manganese components can enhance the activity, efficiency and/or stability of catalysts. The manganese species that provides the enhanced activity, efficiency and/or stability is not certain and may be the component added or that generated either during catalyst preparation or during use as a catalyst. Manganese components include, but are not limited to, manganese acetate, manganese ammonium sulfate, manganese citrate, manganese dithionate, manganese oxalate, manganous nitrate, manganous sulfate, and manganate anion, for example permanganate anion, and the like. To stabilize the manganese component in certain impregnating solutions, it may be necessary to add a chelating compound such as ethylene-diamine-tetraacetic acid (EDTA) or a suitable salt thereof.

The amount of anion promoter may vary widely, for example, from 0.0005 to 2 wt. %, preferably from 0.001 to 0.5 wt. % based on the total weight of the catalyst. Accordingly, the rhenium component is often provided in an amount of at least 5, for example, 10 to 2000, often between 20 and 1000, ppmw calculated as the weight of rhenium based on the total weight of the catalyst. In accordance with the catalyst preparation methods and reaction systems disclosed herein, the amount of anion promoter used for a particular catalyst may depend on a reference property of the catalyst, such as a catalyst physical property, examples of which include carrier specific surface area and silver specific surface area.

It is desirable that the silver and one or more solid-phase promoters be relatively uniformly dispersed on the carrier. A preferred procedure for depositing silver catalytic material and one or more promoters comprises: (1) impregnating a carrier with a solution comprising a solvent or solubilizing agent, silver complex and one or more promoters, and (2) thereafter treating the impregnated carrier to convert the silver compound and effect deposition of silver and the promoter(s) onto the exterior and interior pore surfaces of the carrier. Silver and promoter depositions are generally accomplished by heating the solution-containing carrier at elevated temperatures to evaporate the liquid within the carrier and effect deposition of the silver and promoters onto the interior and exterior carrier surfaces. The temperature of the heating step is high enough to reduce any silver compounds to metallic silver. Impregnation of the carrier is the preferred technique for silver deposition because it utilizes silver more efficiently than coating procedures, the latter being generally unable to effect substantial silver deposition onto the interior surfaces of the carrier. In addition, coated catalysts are more susceptible to silver loss by mechanical abrasion.

Well known methods can be employed to analyze for the amounts of silver and solid-phase promoters deposited onto the alumina carrier. The skilled artisan may employ, for example, material balances to determine the amounts of any of these deposited components. Alternatively, any suitable analytical technique for determining elemental composition, such as X-ray fluorescence (XRF), may be employed to determine the amounts of the deposited components.

While solid-phase promoter concentrations may, in general, vary over a wide range as among different high-efficiency alkylene oxide catalyst batches, it is beneficial to base at least certain promoter concentrations on a reference property of a catalyst that is known to provide acceptable or desirable performance under certain process conditions. Such reference properties may include chemical and physical catalyst properties. In certain preferred examples, the reference property is a physical property of the catalyst. Suitable catalyst physical properties that may serve as a reference property include carrier specific surface area and silver specific surface area. When the catalyst is prepared by impregnation of a carrier, a "batch", at minimum, may be regarded as the amount of catalyst produced in a discrete impregnation step. That is, a "batch" is the smallest unit of production for which it is possible to adjust the target concentrations of catalytic and promoting materials by varying their levels in the impregnating solution. Without wishing to be bound by any theory, it is believed that silver dispersion on the carrier varies with carrier specific surface area and that some catalyst promoters will preferentially bond to the silver, others will preferentially bond to the carrier, and some will bond with equal preference to both silver and the carrier. The portion of a given promoter which bonds to the carrier depends on the type of promoters, the properties of the carrier, and silver dispersion and concentration. Thus, determining the target promoter concentration in accordance with the methods described herein helps maintain a consistent distribution of promoters attached to each of the silver and the carrier, resulting in more consistent performance among batches of catalyst having different values of the catalyst reference properties. As described further below, the target promoter concentrations are used in preparing impregnating solutions which are contacted with the carrier. In practice, it may not be possible to control the impregnation process so tightly that the resulting promoter concentrations on the catalyst equal the target concentrations. Those skilled in the art may employ techniques that account for impregnation efficiencies to identify an impregnation solution promoter concentration that is likely to provide a promoter concentration on the catalyst that is as close to the target concentration value as possible.

In certain methods described herein, a first high efficiency catalyst is defined which comprises a carrier, silver, and a promoting amount of at least one promoter, the at least one promoter comprising rhenium. Some or all of the at least one promoter may be scaled to prepare a second high efficiency catalyst based on a catalyst reference property. Thus, respective target concentration values of one or more of the at least one promoter on the second catalyst are determined based on values of a catalyst reference property for the first and second catalysts and the respective concentrations of those one or more of the at least one promoters on the first catalyst. The second high efficiency catalyst is prepared based on the respective target concentration values on the second catalyst for the one or more of the at least one promoter. In some embodiments, the respective concentrations of the one or more of the at least one promoter on the second catalyst are the respective target concentrations employed in preparing the second catalyst.

An exemplary method by which the second high efficiency catalyst may be prepared based on the respective target concentration value on the second catalyst for the one or more of the at least one promoter will now be described. In accordance with the method, the second catalyst carrier is contacted with an impregnating solution comprising respective amounts of the one or more of the at least one promoter. As will be appreciated by a skilled person, the respective amounts of the one or more of the at least one promoter provided in the impregnating solution are sufficient to deposit the one or more of the at least one promoter at levels corresponding to the respective target concentration values of the one or more of the at least one promoter on the second catalyst. That is, the impregnating solution is preferably prepared with promoter concentrations sufficient to ensure that the finished catalyst contains the desired amounts of silver and the promoters. The required concentrations of silver and/or promoters in the impregnating solution for the given carrier may be calculated from the packing density (grams/cc) and pore volume of the carrier which are either known or readily determined. The relationship can vary depending upon the nature of the carrier, e.g., pore volume may influence the amount of silver deposited from a given solution. For example, in a one-impregnation process used to apply both silver and the promoter(s), the required concentration(s) of promoter(s) in solution may be obtained by dividing the solution silver concentration by the respective ratio(s) of silver to promoter desired in the finished catalyst. As a further example, for embodiments comprising two-impregnation processes in which only silver is added in a first impregnation and both silver and promoter(s) are added in a second impregnation, the required concentration(s) of promoter(s) in solution may be obtained by dividing the solution silver concentration by the ratio of the desired amount of silver added to the catalyst in the second impregnation to the respective amount(s) of the promoter(s) desired in the finished catalyst.

Various relationships may be used to calculate the respective target concentration values of scaled promoters based on values of the catalyst reference property for the first and second catalyst and the promoters' respective concentrations on the first catalyst. One such relationship is a monotonic relationship between the target promoter concentration value and the catalyst reference property. In certain examples, the monotonic relationship is a linear relationship. In yet other examples, the monotonic linear relationship is a non-proportional relationship, or a linear and non-proportional relationship.

In other implementations, the monotonic relationship is a spline consisting of two mathematical formulas, wherein the spline knot is placed at the catalyst reference property value of the first catalyst. An exemplary first one of the two mathematical formulas is represented as follows:

$$CP_{2i}=CP_{1i}(1+A_i(RP_2/RP_1-1)) \qquad (1)$$

wherein i is an index corresponding to a particular promoter, $CP_{1i}$ is the concentration of the ith promoter on the first catalyst, $CP_{2i}$ is the concentration of the ith promoter on the second catalyst, $RP_1$ is the value of the reference property for the first catalyst, $RP_2$ is the value of the reference property for the second catalyst, and $A_i$ is a non-zero scaling multiplier for the ith promoter.

Using the same nomenclature, an example of the second formula is as follows:

$$CP_{2i}=CP_{1i}/(1+A_i(RP_1/RP_2-1)) \qquad (2)$$

In certain implementations, the first and second formulas correspond to different domains for the ratios of the first and second catalyst reference properties and share a common set of scaling multipliers $A_i$. In one preferred embodiment wherein the catalyst reference property is carrier specific surface area, the first formula (equation (1)) is used when $RP_2/RP_1 \geq 1$, and the second formula (equation (2)) is used when $RP_2/RP_1 < 1$, the set of scaling multipliers $A_i$ used with equation (1) also being used with equation (2). In some implementations, the scaled promoters for which equation (1) and/or equation (2) are used comprise a plurality of promoters, and $A_i$ is the same for each promoter of the plurality of promoters, while in other implementations, $A_i$ is different among at least two of the promoters in the plurality of promoters. In particular embodiments, the scaling multiplier $A_i$ for at least one promoter has a value that is not equal to one.

In the case of a defined functional relationship such as that provided by equations (1) and (2), a numeric threshold can be defined to distinguish a "scaled promoter" from a "non-scaled promoter." Thus, in certain examples in which equations (1) and/or (2) are used, "non-scaled promoters" are defined as having a value of the scaling multiplier $A_i$ that is less than 0.2, and "scaled promoters" are correspondingly defined as having a scaling multiplier $A_i$ that is at least 0.2. In certain examples, the scaled promoters used to prepare a high-efficiency alkylene oxide catalyst each have a scaling multiplier value $A_i$ that is preferably at least 0.5, more preferably, at least 0.7, and still more preferably at least 0.75. At the same time, the scaled promoters used to prepare a high-efficiency alkylene oxide catalyst each have a scaling multiplier value $A_i$ that is preferably no greater than 2.00, more preferably no greater than 1.5, and yet more preferably no greater than 1.25.

Another suitable functional relationship for relating promoter concentration values to a catalyst reference property may be represented by the following formula:

$$CP_{2i}=CP_{1i}(RP_2/RP_1)^{\alpha i} \qquad (3)$$

wherein i is an index corresponding to a particular promoter, $CP_{1i}$ is the concentration of the ith promoter on the first catalyst, $CP_{2i}$ is the concentration of the ith promoter on the second catalyst, $RP_1$ is the value of the reference property for the first catalyst, $RP_2$ is the value of the reference property for the second catalyst, and $\alpha i$ is a non-zero scaling exponent for the ith promoter.

In certain situations where equation (3) is used to calculate target promoter concentration values for scaled promoters, each scaled promoter may have the same scaling exponent $\alpha i$, while in other situations at least two of the scaled promoters may have different values of the scaling exponent $\alpha i$. In particular embodiments, the scaling exponent $\alpha i$ for at least one of the scaled promoters has a value that is not equal to one.

In cases where equation (3) is used, non-scaled promoters may be defined as those in which the scaling exponent $\alpha i$ is less than 0.2. Scaled promoters may be defined as those for which the scaling exponent $\alpha i$ is greater than 0.2. Preferred values of the scaling exponent $\alpha i$ for scaled promoters are preferably no greater than 1.5, more preferably no greater than 1.4, and still more preferably no greater than 1.1.

In accordance with the foregoing methods of preparing a high-efficiency alkylene oxide catalyst, in certain preferred embodiments, the scaled promoters (i.e., the "one or more of the at least one promoter") comprise at least one of at least one alkali metal, rhenium, and a rhenium co-promoter. In certain implementations, the at least one alkali metal comprises at least one of cesium, lithium, and sodium. In other implementations, the at least one alkali metal comprises cesium and lithium. In further implementations, the at least one alkali metal comprises cesium, lithium, and sodium.

In additional preferred methods, the at least one scaled promoter consists essentially of each of cesium, lithium, sodium, rhenium, and sulfate. In other preferred methods, the at least one scaled promoter consists of each of cesium, lithium, sodium, rhenium, and sulfate. In further preferred methods, the ratio of cesium/rhenium concentrations in the first catalyst is the same as in the second catalyst.

The scaled rhenium promoters and co-promoters may take any of the various forms described previously. Thus, rhenium may be provided as a metal, a covalent compound, a cation, or an anion. Suitable rhenium co-promoters include sulfur, molybdenum, tungsten, chromium, and mixtures thereof, each of which may be provided as an element, a covalent compound, a cation, or an anion. In certain embodiments, sulfur compounds and sulfate $[SO_4]^{-2}$ are preferred rhenium co-promoters.

In certain preferred examples, another one or more of the at least one promoter used in the catalysts described herein has a corresponding target concentration value on the second catalyst which is not determined based on reference property values of the first and second catalyst. Such promoters may be referred to as "non-scaled" promoters as described previously. In some implementations, the another one or more of the at least one promoter comprises a manganese compound.

For scaled promoters, the determination of target promoter concentration values as described above is performed based on the values of a catalyst reference property for the first and second catalyst. The catalyst reference property may be a chemical or physical property. In preferred embodiments, the reference property is a physical property. Preferred physical catalyst properties that are suitable reference properties include carrier specific surface area, silver specific surface area, and the ratio of silver specific surface area to carrier specific surface area. Carrier specific surface area is defined above based on the BET method and is reported in units such as $m^2/g$.

Silver specific surface area is defined as the area of silver divided by the weight of catalyst. It is preferred that procedures for determining the silver specific area be carried out on an unpromoted catalyst. Particular techniques for determining the silver specific area include oxygen and carbon monoxide chemisorptions, and microscopy coupled with image analysis. For purposes of serving as a reference property, the specific surface area of silver that is accessible to reactants is the most important portion of the silver specific surface area. One particular technique employs selective chemisorption of oxygen using a dynamic pulse technique. Asterios Gavrilidis, et al., Influence of Loading on Metal Surface Area for Silver/Alpha-Alumina Catalysts, *J. Catalysis*, 139(1) at 41-47 (1993). Another technique uses a titration method to determine the number of silver surface atoms, and by extension, the specific silver surface area. M. Boudart, Turnover Rates in Heterogeneous Catalysis, *Chem. Rev.*, Vol. 95 at 661-666 (1995).

The methods described herein are particularly helpful when a catalyst is prepared (e.g., the "second catalyst") which has a significantly different value of the reference property than the catalyst on which it is based (the "first catalyst"). In certain preferred examples, the value of the reference property for the second catalyst (i.e., the second value of the reference property) differs from the value of the reference property for the first catalyst (i.e., the first value of the reference property) by an amount that is no less than five percent (5%), preferably no less than ten percent (10%), and more preferably no less than twenty percent (20%) of the first value of the catalyst reference property.

Catalysts prepared in accordance with the foregoing methods may be used as part of a reaction system. As used herein the term "reaction system" comprises physically distinct portions of high-efficiency, rhenium promoted alkylene oxide catalysts which each receive a common feed gas at a given time. For example, such a reaction system may comprise multiple shell-and-tube reactors sharing a common gas feed, or multiple tubes within a single shell-and-tube reactor. In accordance with this disclosure, a reaction system is provided which comprises at least first and second high-efficiency alkylene oxide catalysts. The first catalyst comprises a carrier, silver, and a promoting amount of at least one promoter, the at least one promoter comprising a rhenium promoter. The second catalyst also comprises a carrier, silver, and a promoting amount of at least one promoter, the at least one promoter comprising a rhenium promoter, such that the respective ratios between the respective concentrations of one or more promoters of the at least one promoter on the second catalyst and the respective concentrations of the one or more promoters of the at least one promoter on the first catalyst are respective functions of a catalyst reference property. That is, for at least one of the at least one promoter on the second catalyst, the ratio between the promoter's concentration on the second catalyst and its concentration on the first catalyst is a function of a catalyst reference property.

The functional relationship between the respective ratios of the respective second catalyst concentrations of the so-scaled promoters to the respective first catalyst concentrations of the same promoters and the reference property may take a variety of forms, including those defined by monotonic functions. In certain examples, the monotonic function is a linear function, while in other examples, it is a non-proportional function, or even a linear and non-proportional function. In yet other examples, the monotonic function is a spline consisting of two mathematical formulas, and the spline knot is placed at the catalyst reference property of the first catalyst.

In one particular implementation, the first mathematical formula of the spline may be obtained by dividing each side of equation (1) (above) by $CP_{1i}$. At the same time, the second mathematical formula of the spline may be obtained by dividing each side of equation (2) (above) by $CP_{1i}$.

As discussed previously, equations (1) and (2) each include a scaling multiplier $A_i$. In certain examples, the scaled promoters (i.e., the one or more promoters of the at least one promoter) comprise a plurality of scaled promoters and the value of the scaling multiplier $A_i$ is the same for each of them, while in other cases at least two of the promoters in the plurality of promoters have different scaling multiplier values. The preferred and exemplary values of $A_i$ are the same for the reaction system as for the methods of preparing a high-efficiency alkylene oxide catalyst described above.

In another example, the monotonic function used to relate the ratio of scaled promoter concentrations to the catalyst reference property is represented by dividing each side of equation (3) by $CP_{1i}$. In certain examples, the scaled promoters (i.e., the one or more promoters of the at least one promoter) comprise a plurality of promoters, and each of them has the same value of the scaling exponent αi, while in other cases at least two of the promoters in the plurality of promoters have scaling exponents that differ from one another. Preferred and exemplary values of the scaling exponent αi are described above with respect to equation (3).

The scaled promoters used to prepare the reaction system catalysts may comprise at least one alkali metal, rhenium, and a rhenium co-promoter as described with respect to the methods of preparing a high-efficiency alkylene oxide catalyst discussed above. Preferred and exemplary alkali metals, rhenium co-promoters, and forms of rhenium are the same for the reaction system as for the methods of preparing a high-efficiency alkylene oxide catalyst described above. The reaction system may also comprise at least one non-scaled promoter (i.e., "another one or more of the at least one promoter") wherein the respective ratios of the respective second catalyst concentrations of the non-scaled promoters to the respective first catalyst concentrations of the same promoters are not functions of the catalyst reference property.

The exemplary and preferred catalyst reference properties for the reaction system catalysts are the same as those used for the methods of preparing a high-efficiency alkylene oxide catalyst described above (e.g., carrier specific surface area, silver specific surface area). The exemplary and preferred quantitative relationships between the first and second reference properties are also the same for the reaction system as for the methods of preparing a high-efficiency alkylene oxide catalyst described above.

It can be useful to define a "promoter scaling factor" as the ratio of a scaled promoter's concentration in a catalyst to the concentration of the same promoter in a reference catalyst:

$$\text{Promoter scaling factor} = CP_{2i}/CP_{1i} \quad (4)$$

In addition, it is useful to normalize the promoter scaling factor based on the values of the reference property for the first and second catalysts. In equation (5), below, the selected reference property is carrier specific surface area:

$$\text{Promoter scaling ratio} = \text{Promoter scaling factor}/(SA_2/SA_1) \quad (5)$$

Thus, when the promoter scaling ratio is 1.0, the scaled promoter concentration varies directly with the ratio $SA_2/SA_1$.

The reaction systems and methods for preparing a high-efficiency alkylene oxide catalyst described herein involve a "first catalyst" with known values of one or more scaled promoter concentrations on the first catalyst and a "second catalyst" in which the one or more scaled promoter concentrations are based on a reference property. In this sense, the first catalyst acts as a "reference catalyst" having properties upon which the second catalyst's properties are based.

In the methods and reaction systems described herein, suitable "first catalysts" may be obtained by preparing several samples of catalysts with a known value of a catalyst reference property that will be used for promoter optimization studies wherein the target concentrations of the promoters are adjusted until a desired level of performance is achieved when the catalysts are operated under a set of standard epoxidation reaction conditions.

In one example, several batches of catalyst are prepared using a reference alpha alumina carrier having a known value of a catalyst reference property, such as carrier specific surface area. The catalyst formulation is optimized by first impregnating different portions of carrier with silver. Each individual portion is then impregnated with varying levels of the promoters preferably in accordance with a statistically designed experimental scheme or other optimization procedure as is well-known in the art. The catalyst may comprise at least one promoter comprising cesium, lithium, sodium, rhenium, sulfate, and manganese. The one or more promoters that will be scaled from among the at least one promoter comprises cesium, lithium, sodium, rhenium, and sulfate. The catalyst may also comprise "another one or more" promoters comprising manganese, which will not be scaled.

Each resulting catalyst batch is used to produce an alkylene oxide from a feed gas comprising alkylene, oxygen, an organic chloride promoter, and one or more ballast gases. The feed gas composition, pressure, and gas hourly space velocity are held constant across all batches. In each case, the reaction temperature is varied to achieve a specified alkylene oxide concentration in the reactor outlet. The efficiency is determined for each batch. The optimum catalyst formulation is selected and defines the "first catalyst" used for determining the respective target concentration values of each of the respective scaled promoters impregnated on the second catalyst. In certain situations, one or more of the respective promoter concentrations used to define the first catalyst may be the respective desired concentrations employed in preparing the first catalyst, while in more preferred cases, they may be the respective actual concentrations as determined by, for example, material balances or analytical measurements of the first catalyst.

As mentioned above, a preferred procedure for depositing silver catalytic material and optionally one or more promoters comprises: (1) impregnating a carrier with a solution comprising a solvent or solubilizing agent, silver complex and optionally one or more promoters, and (2) thereafter treating the impregnated carrier to convert the silver compound to silver metal and effect deposition of silver and the promoter(s) if present onto the exterior and interior pore surfaces of the carrier. Regardless of the particular sequence of impregnation steps, each promoter is added to at least one of the impregnating solutions in amounts (accounting for losses and expected promoter pick-up during impregnation) sufficient to achieve the targeted concentration values (e.g., $CP_{1i}$) for the finished catalyst which are calculated using the methods described herein. The amount of silver pick up by the carrier is estimated using known estimation techniques to determine the amount (mass or moles) of each promoter necessary to achieve the targeted promoter concentrations (e.g., parts per million by weight, or micromoles per gram of catalyst).

Accordingly, in a preferred embodiment, the different catalyst batches are each prepared by co-impregnation of the different portions of carrier with silver and promoters in a solution, followed by draining and calcining to effect deposition of the desired catalyst components. In an especially preferred embodiment, a large portion of carrier is first impregnated with silver in a first impregnating solution, drained, and calcined to effect deposition of the silver, and subsequently smaller portions of the resulting silver catalyst are individually impregnated a second time with respective second impregnating solutions comprising silver and varying levels of the promoters in accordance with a statistically designed experimental scheme.

The silver solution used to impregnate the carrier is preferably comprised of a silver compound in a solvent or complexing/solubilizing agent such as the silver solutions disclosed in the art. The particular silver compound employed may be chosen, for example, from among silver complexes, silver nitrate, silver oxide, or silver carboxylates, such as silver acetate, oxalate, citrate, phthalate, lactate, propionate, butyrate and higher fatty acid salts. Silver oxide complexed with amines is another form of silver that may be used. One preferred silver impregnation solution comprises a soluble/colloidal amine oxalate complex with silver.

As with the silver deposition, soluble salts of the scaled and non-scaled promoters may be dissolved in one or more solvents and/or solubilizing agents and deposited, preferably by impregnation, onto the carrier. The sequence of impregnating or depositing the surfaces of the carrier with silver and the various promoters (e.g., Cs, Li, Na, Re, $[SO_4]^{-2}$, and Mn) may vary. Thus, impregnation and deposition of silver and the various promoters, may be effected coincidentally or sequentially. One or more of the promoters may be deposited prior to, during, or subsequent to silver deposition to the carrier. Any of the various promoters may be deposited together or sequentially.

For example, the carrier may be impregnated in a sequence of two or more "dips" in an impregnating solution. In one example, the carrier is first dipped into a silver complex solution that is free of the promoters, treated to effect deposition of the silver, and is then dipped into a silver complex solution that includes the promoters. In another example, some or all of the promoters may be introduced along with the silver complex in the first dip (impregnation).

In another example, silver may be deposited first followed by the coincidental or sequential deposition of cesium, lithium, sodium, rhenium, $[SO_4]^{-2}$, and manganese. Alternatively, sodium may be deposited first followed by coincidental or sequential deposition of silver and the remaining promoters; or alternatively, cesium may be deposited first followed by coincidental or sequential deposition of silver and the remaining promoters. If two or more impregnations are employed, the impregnated carrier is typically dried, or calcined and/or roasted between each successive impregnation to ensure deposition of the metals onto the carrier.

In another exemplary method, the carrier is impregnated with a silver containing solution (such as a silver complex solution) followed by flash calcination. The carrier is then impregnated a second time with a silver containing solution followed by flash calcination. The promoters are then sequentially impregnated (without silver) in a third impregnation step followed by flash calcination.

In one specific exemplary method, the high-efficiency alkylene oxide catalysts described herein are prepared by vacuum impregnation of the carrier with silver-amine-oxalate solutions prepared as described under "Catalyst Preparation" in U.S. Patent Application Publication No. 2009/177000.

The catalysts described herein are high-efficiency catalysts useful for reacting alkylenes and oxygen to yield alkylene oxides, and the methods of making catalysts described herein are believed to improve the consistency of certain aspects of catalyst performance, for example, catalyst activity, among catalyst batches that differ as to a selected catalyst reference property, for example, catalyst physical properties such as carrier specific surface area. In exemplary processes of making alkylene oxides using these catalysts, oxygen may be provided as substantially pure oxygen or air. If pure oxygen is used, ballast gases or diluents such as nitrogen or methane may also be included to maintain the oxygen concentration below the maximum level allowed by flammability considerations. The concentration of oxygen in the reactor feed stream may vary over a wide range, and in practice, flammability is generally the limiting factor for oxygen concentration. Generally, the oxygen concentration in the reactor feed will be at least one (1) mole percent, preferably at least two (2) mole percent, and still more preferably at least four (4) mole percent. The oxygen concentration will generally be no more than fifteen (15) mole percent, preferably no more than twelve (12) mole percent, and even more preferably no more than nine (9) mole percent. The ballast gas (e.g., nitrogen or methane) is generally from 50 mole percent to 80 mole percent of the total composition of reactor feed stream. Methane ballast gas is preferred over nitrogen because, due to its higher heat capacity, it facilitates the use of higher oxygen concentrations in the cycle, and therefore, improves both activity and efficiency.

In certain exemplary processes, the concentration of oxygen in the reactor feed is set at a pre-selected maximum value which is no greater than an amount of oxygen that would form a flammable mixture with the components of reactor feed at the prevailing process conditions (the "oxygen flammability concentration"). In other embodiments, the maximum oxygen concentration is no greater than a pre-defined percentage of the oxygen flammability concentration (e.g., the maximum oxygen concentration is no greater than 95% of the oxygen flammability concentration and preferably no greater than 90% of the oxygen flammability concentration). In certain further embodiments, the maximum oxygen concentration and/or the oxygen flammability concentration is determined based on at least one variable selected from the group consisting of reaction temperature, pressure, alkylene concentration, alkylene oxide concentration, ballast gas concentration, and carbon dioxide concentration in the reactor feed.

The concentration of olefin in the reactor feed stream may vary over a wide range. However, it is preferably at least eighteen (18) mole percent and more preferably at least twenty (20) mole percent. The concentration of olefin in the reactor feed stream is preferably no greater than 50 mole percent, and more preferably is no greater than 40 mole percent.

The carbon dioxide concentration in the reactor feed stream has a large adverse effect on the efficiency, activity and/or stability of the high-efficiency catalyst. Carbon dioxide is produced as a reaction by-product and may also be introduced with other inlet reaction gases as an impurity. In commercial ethylene epoxidation processes, at least part of the carbon dioxide is removed continuously in order to control its concentration to an acceptable level in the cycle. The carbon dioxide concentration in the reactor feed is generally no more than 5 mole percent and preferably no more than 3 mole percent of the total composition of reactor feed. Water is also a reaction by-product (or may be present in a recycle stream, for example, when a water-based absorber is used to treat the reactor product stream), and may be present in the feed gases in concentrations that are preferably from 0 to no more than three (3) mole percent.

The gas phase promoter is generally a compound that enhances the efficiency and/or activity of the process for producing the desired alkylene oxide. Preferred gas phase promoters include organic chlorides. More preferably, the gas phase promoter is at least one selected from the group consisting of methyl chloride, ethyl chloride, ethylene dichloride, vinyl chloride, and mixtures thereof. Ethyl chloride and ethylene dichloride are most preferred. Using chlorohydrocarbon gas phase promoters as an example, it is believed that the ability of the promoter to enhance the performance (e.g., efficiency and/or activity) of process for making the desired alkylene oxide depends on the extent to which the gas phase promoter chlorinates the surface of the catalyst, for example, by depositing particular chlorine species such as atomic chlorine or chloride ions on the catalyst or in the gas phase above the catalyst. However, hydrocarbons lacking chlorine atoms are believed to strip chlorides from the catalyst, and therefore, detract from the overall performance enhancement provided by the gas phase promoter. Discussions of this phenomenon may be found in Berty, "Inhibitor Action of Chlorinated Hydrocarbons in the Oxidation of Ethylene to Ethylene Oxide," *Chemical Engineering Communications*, Vol. 82 (1989) at 229-232 and Berty, "Ethylene Oxide Synthesis," *Applied Industrial Catalysis*, Vol. I (1983) at 207-238. Paraffinic compounds, such as ethane or propane, are believed to be especially effective at stripping chlorides from the catalyst. However, olefins such as ethylene and propylene are also believed to act to strip chlorides from the catalyst. Some of these hydrocarbons may also be introduced as impurities in the ethylene (olefin) feed or may be present for other reasons (such as the use of a recycle stream). Typically, the preferred concentration of ethane in the reactor feed, when present, is from 0 to 2 mole percent. Given the competing effects of the gas phase promoter and the non-halogenated, non-promoting hydrocarbons in the reactor feed stream, it is convenient to define an "overall catalyst chloriding effectiveness value" that represents the net effect of gas phase species in chloriding the catalyst. In the case of organic chloride gas-phase promoters, the overall catalyst chloriding effectiveness can be defined as the dimensionless quantity Z* and represented by the following formula:

$$Z* = \frac{\text{ethyl chloride equivalent } (ppmv)}{\text{ethane equivalent (mole percent)}} \quad (6)$$

wherein the ethyl chloride equivalent is the concentration in ppmv of ethyl chloride that provides the same catalyst chloriding effectiveness of the organic chlorides present in the reactor feed stream at the concentrations of the organic chlorides in the reactor feed stream; and the ethane equivalent is the concentration of ethane in mole percent that provides the same catalyst dechloriding effectiveness of the non-chloride containing hydrocarbons in the reactor feed stream at the concentrations of the non-chloride containing hydrocarbons in the reactor feed stream.

If ethyl chloride is the only gaseous chloride-containing promoter present in reactor feed stream, the ethyl chloride equivalent (i.e., the numerator in equation (6)) is the ethyl chloride concentration in ppmv. If other chlorine-containing promoters (specifically vinyl chloride, methyl chloride or ethylene dichloride) are used alone or in conjunction with ethyl chloride, the ethyl chloride equivalent is the concentration of ethyl chloride in ppmv plus the concentrations of the other gaseous chloride-containing promoters (corrected for their effectiveness as a promoter as compared to ethyl chloride). The relative effectiveness of a non-ethyl chloride promoter can be measured experimentally by replacing ethyl chloride with the other promoter and determining the concentration needed to obtain the same level of catalyst performance provided by ethyl chloride. As a way of further illustration, if the required concentration of ethylene dichloride at the reactor inlet is 0.5 ppmv to realize equivalent effectiveness in terms of catalyst performance provided by 1 ppmv ethyl chloride, then the ethyl chloride equivalent for 1 ppmv ethylene dichloride would be 2 ppmv ethyl chloride. For a hypothetical feed of 1 ppmv ethylene dichloride and 1 ppmv ethyl chloride, the ethyl chloride equivalent in the numerator of Z* would then be 3 ppmv. As a further example, it has been found that for certain catalysts methyl chloride has 10 times less the chloriding effectiveness of ethyl chloride. Therefore, for such catalysts the ethyl chloride equivalent for a given concentration of methyl chloride in ppmv is 0.1× (methyl chloride concentration in ppmv). It has also been found that for certain catalysts, vinyl chloride has the same chloriding effectiveness as ethyl chloride. Therefore, for such catalysts the ethyl chloride equivalent for a given concentration of vinyl chloride in ppm is 1.0× (vinyl chloride concentration in ppmv). When more than two chlorine-containing promoters are present in reactor feed stream, which is often the case in commercial ethylene epoxidation processes, the overall ethyl chloride equivalent is the sum of the corresponding ethyl chloride equivalents for each individual chlorine-containing promoter that is present. As an example, for a hypothetical feed of 1 ppmv ethylene dichloride, 1 ppmv ethyl chloride, and 1 ppmv vinyl chloride, the ethyl chloride equivalent in the numerator of Z* would be 2*1+1+1*1=4 ppmv.

The ethane equivalent (i.e., the denominator in equation (6)) is the concentration of ethane in mole percent in reactor feed stream plus the concentration of the other hydrocarbons effective in removing chloride from the catalysts, corrected for their effectiveness for dechlorination relative to ethane. The relative effectiveness of ethylene compared to ethane can be measured experimentally by determining the inlet ethyl chloride equivalent concentration that provides the same level of catalyst performance for a feed comprising both ethylene and ethane as compared to the same feed with the same ethylene concentration but a specific ethyl chloride equivalent concentration and no ethane. As a way of further illustration, if with a feed composition comprising an ethylene concentration of 30.0 mole percent and an ethane concentration of 0.30 mole percent, a level of 6.0 ppm ethyl chloride equivalents is found to provide the same level of catalyst performance as 3.0 ppm ethyl chloride equivalents with a similar feed composition but lacking ethane, then the ethane equivalent for 30.0 mole percent ethylene would be 0.30 mole percent. For an inlet reactor feed having 30.0 mole percent ethylene and 0.3 mole percent ethane, the ethane equivalent will then be 0.6 mole percent. As another illustration, it has been found that for certain catalysts methane has 500 times less the dechloriding effectiveness of ethane. Thus, for such catalysts the ethane equivalent for methane is 0.002× (methane concentration in mol percent). For a hypothetical inlet reactor feed having 30.0 mole percent ethylene and 0.1 mole percent ethane, the ethane equivalent then will be 0.4 mole percent. For an inlet reactor feed having 30.0 mole percent ethylene, 50 mole percent methane, and 0.1 mole percent ethane, the ethane equivalent then will be 0.5 mole percent. The relative effectiveness of hydrocarbons other than ethane and ethylene can be measured experimentally by determining the inlet ethyl chloride equivalent concentrations required to achieve the same catalyst performance for a feed comprising the hydrocarbon of interest at its concentration in the feed at two different concentrations of ethane in the feed. If a hydrocarbon compound is found to have a very small dechloriding effect and is also present in low concentrations, then its contribution to the ethane equivalent concentration in the Z* calculation may be negligible.

Thus, given the foregoing relationships, in the case where the reactor feed stream includes ethylene, ethyl chloride, ethylene dichloride, vinyl chloride, and ethane, the overall catalyst chloriding effectiveness value of the process can be defined as follows:

$$Z* = \frac{(ECL + 2*EDC + VCL)}{(C_2H_6 + 0.01*C_2H_4)} \quad (7)$$

wherein ECL, EDC, and VCL are the concentrations in ppmv of ethyl chloride ($C_2H_5Cl$), ethylene dichloride (Cl—$CH_2$—$CH_2$—Cl), and vinyl chloride ($H_2C$=CH—Cl), respectively, in the reactor feed stream. $C_2H_6$ and $C_2H_4$ are the concentrations in mole percent of ethane and ethylene, respectively, in the reactor feed stream. It is important that the relative effectiveness of the gaseous chlorine-containing promoter and the hydrocarbon dechlorinating species also be measured under the reaction conditions which are being used in the process. Z* will preferably be maintained at a level that is no greater than 20 and which is most preferably no greater than 15. Z* is preferably at least 1.

Although the gaseous chlorine-containing promoter may be supplied as a single species, upon contact with the catalyst, other species may be formed leading to a mixture in the gas phase. Consequently, if the reaction gases are recycled such as via a recycle stream, a mixture of species will be found in the inlet of the reactor. In particular, the recycled reaction gases at the inlet may contain ethyl chloride, vinyl chloride, ethylene dichloride and methyl chloride, even though only ethyl chloride or ethylene dichloride is supplied to the system. The concentrations of ethyl chloride, vinyl chloride, and ethylene dichloride must be considered in calculating Z*. In certain embodiments of the methods of making a high-efficiency alkylene oxide catalyst and the reaction systems described herein, the respective concentrations of one or more of at least one promoter are scaled on a second catalyst based on values of a reference property for the second catalyst and a first catalyst to provide comparable Z* responses and similar optimum values of Z* at particular reaction conditions among different catalyst batches having different values of the catalyst reference property.

The order in which the inlet gases (alkylene oxide and oxygen and ballast gas) and gas phase promoter are mixed together is not critical, and they may be mixed simultaneously or sequentially. The order of mixing of the gaseous components of the process may be chosen for convenience and/or for safety reasons. For example, oxygen is generally added after the ballast gas for reasons of safety. However, the gas phase promoter should be present in the reactor feed stream as it is introduced to the solid catalyst in the reactor.

The reactor used to make alkylene oxide from the high-efficiency catalysts described herein may be of a variety of reactor types, including, fixed bed tubular reactors, continuous stirred tank reactors (CSTR), and fluid bed reactors, a wide variety of which are well known to those skilled in the art and need not be described in detail herein. The desirability of recycling unreacted feed, or employing a single-pass system, or using successive reactions to increase ethylene conversion by employing reactors in series arrangement can also be readily determined by those skilled in the art. The particular mode of operation selected is usually dictated by process economics.

The epoxidation reaction is generally exothermic. Thus, a coolant system (e.g., a cooling jacket or a hydraulic circuit with a coolant fluid such as a heat transfer fluid or boiling water) is provided to regulate the temperature of the reactor. The heat transfer fluid can be any of several well-known heat transfer fluids, such as tetralin (1,2,3,4-Tetrahydronaphthalene). The epoxidation reaction is carried out at a temperature that is preferably at least 200° C., more preferably at least 210° C., and most preferably at least 220° C. Reaction temperatures of no more than 300° C. are preferred, and reaction temperatures of no more than 290° C. are more preferred. Reaction temperatures of no more than 280° C. are most preferred. The reactor pressure is selected based on the desired mass velocity and productivity and ranges generally from 5 atm (506 kPa) to 30 atm (3.0 MPa). The gas hourly space velocity (GHSV) is preferably greater than 3000 h$^{-1}$, more preferably greater than 4,000 hr$^{-1}$, and most preferably greater than 5,000 hr$^{-1}$.

It should be noted that the terms "reaction temperature," "epoxidation temperature" or "epoxidation reaction temperature" refer to any selected temperature(s) that are directly or indirectly indicative of the catalyst bed temperature. In certain embodiments, the reaction temperature may be a catalyst bed temperature at a specific location in the catalyst bed. In other embodiments, the reaction temperature may be a numerical average of several catalyst bed temperature measurements made along one or more catalyst bed dimensions (e.g., along the length). In additional embodiments, the reaction temperature may be the reactor outlet gas temperature. In further embodiments, the reaction temperature may be the reactor inlet or outlet coolant temperature.

EXAMPLES

Several catalysts are prepared which comprise silver, an alpha alumina carrier, and the promoters Cs, Li, Na, Re, $[SO_4]^{-2}$, and Mn. The alpha-alumina carriers employed are of the fluoride-mineralized, platelet-containing type. The catalyst preparation technique is as follows. The carrier is vacuum impregnated with a first impregnation silver solution typically containing 30 weight percent silver oxide, 18 weight percent oxalic acid, 17 weight percent ethylenediamine, 6 weight percent monoethanolamine, and 27 weight percent distilled water. The first impregnation solution is typically prepared by (1) mixing 1.14 parts of ethylenediamine (high purity grade) with 1.75 parts of distilled water; (2) slowly adding 1.16 parts of oxalic acid dihydrate (reagent grade) to the aqueous ethylenediamine solution such that the temperature of the solution does not exceed 40° C., (3) slowly adding 1.98 parts of silver oxide, and (4) adding 0.40 parts of monoethanolamine (Fe and Cl free).

The carrier is impregnated in an appropriately sized glass or stainless steel cylindrical vessel which is equipped with suitable stopcocks for impregnating the carrier under vacuum. A suitable separatory funnel which is used for containing the impregnating solution is inserted through a rubber stopper into the top of the impregnating vessel. The impregnating vessel containing the carrier is evacuated to approximately 1-2" mercury absolute for 10 to 30 minutes, after which the impregnating solution is slowly added to the carrier by opening the stopcock between the separatory funnel and the impregnating vessel. After all the solution empties into the impregnating vessel (approximately 15 seconds), the vacuum is released and the pressure returned to atmospheric. Following addition of the solution, the carrier remains immersed in the impregnating solution at ambient conditions for 5 to 30 minutes, and is thereafter drained of excess solution for 10 to 30 minutes.

The silver-impregnated carrier is then roasted as follows to effect reduction of silver on the catalyst surface. The impregnated carrier is spread out in a single layer on stainless steel wire mesh trays then placed on a stainless steel belt (spiral weave) and transported through a 2"×2" square heating zone for 2.5 minutes, or equivalent conditions are used for a larger belt operation. The heating zone is maintained at 500° C. by passing hot air upward through the belt and the catalyst particles at the rate of 266 standard cubic feet per hour (SCFH). After being roasted in the heating zone, the catalyst is cooled in the open air to room temperature and weighed.

Next, the silver-impregnated carrier is vacuum impregnated with a second silver impregnation solution containing both the silver oxalate amine solution and the catalyst solid-phase promoters. The second impregnation solution is composed of all of the drained solution from the first impregnation plus a fresh aliquot of the first solution, or a new solution is used. The promoters, added with stirring in order to solubilize them, are added with the goal of achieving the desired target levels on the finished catalysts. The impregnation, draining and roasting steps for this second impregnation are carried out analogously to the first impregnation. The twice-impregnated carrier, that is the finished catalyst, is again weighed. Based upon the weight gain of the carrier in the second impregnation, the weight percent of silver is calculated. The concentration of the promoters are calculated, assuming a similar rate of deposition for the promoters as for the silver. In some cases, the preparation of a catalyst is carried out on a larger or smaller scale than that described here using suitable scale up or scale-down of equipment and methods.

Using a design of experiment technique, various batches of catalyst are prepared using the foregoing technique with varying amounts of at least one promoter comprising Cs, Li, Na, Re, sulfate, and Mn. Each batch is used to produce ethylene oxide from a feed gas comprising ethylene, oxygen, one or more organic chloride gas phase promoters, and a ballast gas. The feed gas composition is held constant during the testing of all batches, except for the gas-phase chloride promoters, which are adjusted to maximize efficiency at the target conditions, and the reaction temperature is adjusted to achieve an ethylene oxide reactor outlet concentration of 2.0 mol %. The optimum solid-phase promoter concentrations are then selected. The three batches of reference catalyst, R-1, R-2, and R-3 are prepared in the same manner using these optimum promoter concentrations as the target promoter concentrations, using carriers having specific surface areas in the range 1.01-1.03 m²/g. Each reference catalyst R-1, R-2, and R-3 has the following target concentrations of the one or more of the least one promoter (i.e., the scaled promoters) by weight: cesium, 558 ppm; lithium, 29 ppm; sodium, 37 ppm, rhenium, 391 ppm, and sulfate, 134 ppm.

The batches of catalyst also include another one or more of the at least one promoter that is not scaled, which comprises manganese at a concentration of 115 ppm.

Additional catalysts are then formulated using carriers C-1 to C-3 having the following properties:

TABLE 1

| Carrier Number | Specific Surface Area (m²/g) | Total Pore Volume (ml/g) |
|---|---|---|
| C-1 | 1.07 | 0.69 |
| C-2 | 1.19 | 0.70 |
| C-3 | 1.25 | 0.70 |

Each of the carriers C-1 to C-3 has a greater specific surface area than those of the carriers for the reference catalysts. Thus, $SA_2/SA_1$ is greater than 1. Using a scaling multiplier $A_i$ of 0.75 and a carrier specific surface area of 1.0 m²/g for the reference property of the first catalyst, $RP_1$, equation (1) is used to calculate the target concentrations of the scaled promoters Cs, Li, Na, Re, and sulfate for each carrier. In contrast, the target concentration of Mn is held fixed at 115 ppm.

The promoter-scaled catalysts are identified in Table 2 below with the designation "S-X" (indicating that at least one promoter is scaled) wherein "S" refers to "scaled" and X is a number. Comparative catalysts are prepared using the carriers C-1 to C-3 without making promoter concentration adjustments based on the surface area of the carrier. These catalysts are identified with the designation "NS-X" (indicating that none of the promoters are scaled) wherein "NS" refers to "non-scaled" and X is a number.

TABLE 2

| Cat. No. | SA (m2/g) | A | PSF[1] | PSR[2] | Cs (ppm) | Li (ppm) | Na (ppm) | Re (ppm) | $[SO_4]^{-2}$ (ppm) | Mn (ppm) |
|---|---|---|---|---|---|---|---|---|---|---|
| S-1 | 1.25 | 0.75 | 1.19 | 0.95 | 663 | 34 | 44 | 464 | 159 | 115 |
| S-2 | 1.19 | 0.75 | 1.14 | 0.96 | 638 | 33 | 42 | 447 | 153 | 115 |
| S-3 | 1.07 | 0.75 | 1.05 | 0.98 | 587 | 31 | 39 | 412 | 141 | 115 |
| NS-1 | 1.25 | 0 | 1 | 0.80 | 558 | 29 | 37 | 391 | 134 | 115 |
| NS-2 | 1.19 | 0 | 1 | 0.84 | 558 | 29 | 37 | 391 | 134 | 115 |
| NS-3 | 1.07 | 0 | 1 | 0.93 | 558 | 29 | 37 | 391 | 134 | 115 |

[1] PSF = Promoter Scaling Factor = promoter concentration/promoter reference concentration. Wherein the promoter reference concentrations by weight are: cesium, 558 ppm; lithium, 29 ppm; sodium, 37 ppm, rhenium, 391 ppm, and sulfate, 134 ppm.
[2] PSR = Promoter Scaling Ratio = PSF/(carrier specific surface area/reference carrier specific surface area)

The effect of varying the scaling multiplier $A_i$ is determined by preparing modified versions of the S-1 to S-3 catalysts with scaling multiplier values of 0.5 and 1.25. The resulting formulations are provided in Table 3. The formulations are identified with the designation "VS-X" wherein "VS" refers to "varied scaling" and X is a number:

TABLE 3

| Cat. No. | SA (m2/g) | A | PSF[1] | PSR[2] | Cs (ppm) | Li (ppm) | Na (ppm) | Re (ppm) | $[SO_4]^{-2}$ (ppm) | Mn (ppm) |
|---|---|---|---|---|---|---|---|---|---|---|
| VS-1 | 1.19 | 0.5 | 1.10 | 0.92 | 611 | 32 | 41 | 428 | 147 | 115 |
| VS-2 | 1.25 | 0.5 | 1.13 | 0.90 | 628 | 33 | 42 | 440 | 151 | 115 |
| VS-3 | 1.19 | 1.25 | 1.24 | 1.04 | 691 | 36 | 46 | 484 | 166 | 115 |
| VS-4 | 1.25 | 1.25 | 1.31 | 1.05 | 732 | 38 | 49 | 513 | 176 | 115 |
| VS-5 | 1.07 | 1.25 | 1.09 | 1.02 | 607 | 32 | 40 | 425 | 146 | 115 |

[1] PSF = Promoter Scaling Factor = promoter concentration/promoter reference concentration. Wherein the promoter reference concentrations by weight are: cesium, 558 ppm; lithium, 29 ppm; sodium, 37 ppm, rhenium, 391 ppm, and sulfate, 134 ppm.
[2] PSR = Promoter Scaling Ratio = PSF/(carrier specific surface area/reference carrier specific surface area)

Example 1

Catalysts NS-1 to NS-3, S-1, and S-2 in Table 2 are tested as follows: An amount of 0.7 g of crushed catalyst (mesh size 30-50) is mixed with Denstone® 80 inert in a 1:1 by weight ratio and loaded into a microreactor. Quartz wool is introduced at both ends of the catalyst bed and a stainless steel rod with 2.5 mm diameter and 100 mm length is introduced at the bottom end to hold the catalyst in place. After successful leak testing the reactors are heated up in a flow of $N_2$ to a target reaction temperature of 240° C. Once the target temperature is achieved, the reactors are switched to the reactant feed. The reactor feed concentration used to evaluate the initial performance of the catalysts is 30 mol % $C_2H_4$; 8 mol % $O_2$; 1.5 mol % $CO_2$; 0.7 mol % $C_2H_6$; ethyl choride as described below; and the balance $N_2$. The concentration of ethyl chloride is initially set to provide a target Z* value of 1.5. Subsequently, the ethyl chloride concentration is increased to provide an increase of 0.5 Z* units every 12 hours. This is continued until the efficiency of all the catalysts reaches a maximum and starts declining. If the peak (maximum) efficiency is not achieved at 2 mol % outlet ethylene oxide then the reaction temperature of that catalyst is adjusted such that during another Z* traverse the peak efficiency will be realized at or close to 2 mol % outlet ethylene oxide. In making these temperature adjustments, the following relation is used: An increase in ethylene oxide outlet concentration of 1 mol % requires an increase in reaction temperature of 16.6° C. The gas hourly space velocity (GHSV) is approximately 10,000 h$^{-1}$ based on the packing density of the whole pill catalyst and the reactor pressure is kept at 19.5 barg (1.95 MPa).

Table 4 provides activity data for the catalysts with scaled promoter concentrations (S-1, S-2) and three that are not promoter-scaled (NS-1, NS-2, NS-3) relative to reference catalyst R-2 from day 4 of the run. Z* is 3.0 on day 4. When normalized to a reactor outlet ethylene oxide concentration of 2 mol %, the reactor temperature data indicates that catalysts S-1 and S-2 show the lowest activity deviations relative to R-2 while still obtaining comparable or better efficiency toward ethylene oxide (when normalized to the same 2 mol % reactor outlet concentration of ethylene oxide).

5 and are the reactor outlet ethylene oxide concentrations corresponding to the maximum selectivity values on day 9. The relative difference in activity between each catalyst and the reference catalyst R-3 is determined in accordance with the following relationship:

$$\Delta Activity = 100(oEO - oEO_{R-3})/oEO_{R-3} \quad (8)$$

wherein, oEO=the reactor outlet ethylene oxide concentration of the catalyst of interest, and $oEO_{R-3}$ is the reactor outlet ethylene oxide concentration for reference catalyst R-3.

As the table indicates, catalysts S-1 and S-2 show the lowest activity deviation relative to R-3. A scaling multiplier value of 0.75 achieves the best match in activity. A scaling multiplier ($A_i$) value of 0.5 also provides good performance, but at a scaling factor of 1.25, the relative activity deteriorates significantly.

TABLE 4

| Catalyst | SA (m$^2$/g) | Ai | Actual Eff[1] | Actual Outlet EO[2] (mol %) | Eff. @ 2 mol % EO[3] | Rx T[4] (° C.) | Rx T @ 2 mol % EO[5] |
|---|---|---|---|---|---|---|---|
| R-2 | 1.03 | — | 84.6 | 1.91 | 84.3 | 240 | 241 |
| S-1 | 1.25 | 0.75 | 86.7 | 1.97 | 86.6 | 240 | 240 |
| S-2 | 1.19 | 0.75 | 86.4 | 1.96 | 86.3 | 240 | 241 |
| NS-1 | 1.25 | 0 | 83.5 | 2.25 | 84.3 | 235 | 231 |
| NS-2 | 1.19 | 0 | 83.4 | 2.33 | 84.4 | 233 | 228 |
| NS-3 | 1.07 | 0 | 83.6 | 2.30 | 84.5 | 240 | 236 |

[1]Eff = efficiency toward ethylene oxide
[2]EO = ethylene oxide
[3]Refers to the efficiency toward ethylene oxide corrected to a reactor outlet concentration of 2 mole percent ethylene oxide using the relationship that a 1 mol % increase in outlet ethylene oxide concentration results in a 3% reduction in efficiency.
[4]Reaction temperature
[5]Reaction temperature corrected to a reactor outlet concentration of 2 mole percent ethylene oxide using the relationship that a 1 mol % increase in outlet ethylene oxide concentration requires a reaction temperature increase of 16.6° C.

Example 2

Catalysts NS-1, S-1, and S-2 in Table 2 and catalysts VS-1 to VS-5 in Table 3 are tested as follows. An amount of 40 ml of each catalyst is loaded into a Rotoberty reactor and subjected to a feed gas comprising ethylene (30 mol %), ethane (0.6 mol %), oxygen (8 mol %) and CO$_2$ (2 mol %). The reactor pressure is maintained at 285 psig (2 MPa). The feed gas volumetric flow rate is maintained at 11.68 SCFH (measured as nitrogen; 5.5 standard liters per minute), and the gas hourly space velocity is maintained at 6900 h$^{-1}$. Ethyl chloride is also included in the feed gas to provide desired values of the overall catalyst chloriding value, Z*. The start-up reaction temperature is 235° C., and the start-up value of Z* is 1.5. The reaction temperature is held constant throughout the run, and Z* is increased one unit per day by increasing the concentration of ethyl chloride such that on day 5 the ethyl chloride concentration in the reactor feed is 4.95 ppm, and Z* is 5.5.

On day 6, the ethyl chloride concentration is held at 4.95 ppm. From day 7-10 the ethyl chloride concentration is decreased stepwise such that Z* decreases by one unit per day from 5.5 to 1.5.

Table 5 provides activity data for the catalysts with scaled promoter concentrations (S-1 to S-2 and VS-1 to VS-5) and one that is not promoter-scaled (NS-1) relative to that of reference catalyst R-3 from day 9 of the run when the reaction temperature is 235° C., Z* is 2.5, and maximum selectivity is achieved. The values of actual reactor outlet ethylene oxide concentration (mol %) are reported in Table

TABLE 5

| Catalyst | SA (m$^2$/g) | $A_i$ | Actual Outlet EO (mol %) | Δ Activity relative to R-3 |
|---|---|---|---|---|
| R-3 | 1.0 | — | 2.00 | 0 |
| S-1 | 1.25 | 0.75 | 1.97 | −2 |
| S-2 | 1.19 | 0.75 | 1.98 | −1 |
| VS-1 | 1.19 | 0.5 | 2.04 | 2 |
| VS-2 | 1.25 | 0.5 | 2.10 | 5 |
| VS-3 | 1.19 | 1.25 | 1.59 | −21 |
| VS-4 | 1.25 | 1.25 | 1.62 | −19 |
| VS-5 | 1.07 | 1.25 | 1.63 | −19 |
| NS-1 | 1.25 | 0 | 2.4 | 20 |

In general, groups of catalysts with a different carrier specific surface area and the same non-zero scaling multiplier value achieve comparable performance. The results indicate that linearly scaling the catalyst concentrations of the scaled promoters cesium, lithium, sodium, rhenium, and sulfate while not scaling the concentration of the non-scaled promoter manganese achieves an acceptable degree of consistency in activity irrespective of carrier specific surface area when the scaling multiplier is maintained in the range 0.5 to 1.25. Without wishing to be bound by any theory, manganese is believed to sustain active silver and to improve long term catalyst stability. However, it is also believed to detrimentally affect efficiency at high levels. Thus, in certain examples, it is preferably not scaled (i.e., it is not varied as a function of carrier specific surface area or $A_i$ is set to less than 0.2 in equations (1) and (2)).

Example 3

Catalysts S-1 to S-3 and NS-1 to NS-3 and reference catalyst R-1 are tested in a High Pressure Reactor Assembly Module (HPRAM) II system provided by the Foundation for Scientific and Industrial Research at the Norwegian Institute of Technology. The reactor feed gas comprises ethylene (34 mol %), ethane (0.29-0.58 mol %), oxygen (7.2 mol %), CO2 (2.4 mol %), ethyl chloride (1.3-5.0 ppm by volume) and methane (10 mol %), with the balance being helium. The reactor temperature is maintained at 231° C.

During each run, the reactor is charged with 100 mg of the catalyst (30/50 mesh) without inert diluents. The reactor is heated under helium flow, and all feed gases except oxygen are fed to it. Approximately 2-3 minutes after introducing the other feed gases to the reactor, oxygen is introduced. The target gas hourly space velocity is 9000 $h^{-1}$ for each catalyst, which is calculated based on the actual weight of powders and the bulk packing density (0.761 g/ml) for full pellets of the catalysts.

After an activation period of 48 hours, Z* is traversed through a range of values for each catalyst and the ethylene oxide concentration in the reactor outlet is measured multiple times at each Z* value. During the 48 hour activation period, Z* is maintained at 2.1. Thereafter, Z* is adjusted to values of 1.8, 2.4, 3.3, 4.1, 5.7. 6.9, and 8.6, each of which is maintained for 14 hours. Reaction temperature, gas hourly space velocity, and feed gas composition are otherwise held constant during this segment of each run. The same procedure is then repeated at a reaction temperature of 236° C.

Using curve fitting techniques, a second order polynomial is generated for each reaction temperature that relates efficiency toward ethylene oxide for each catalyst to Z*. A similar fit is made for outlet ethylene oxide concentrations versus Z*. By taking the first derivative of the efficiency polynomial and setting it equal to zero, efficiency-maximizing Z* values at that temperature and the efficiency values and reactor outlet ethylene oxide concentration values to which they correspond can be determined for each catalyst.

Figure 1B:
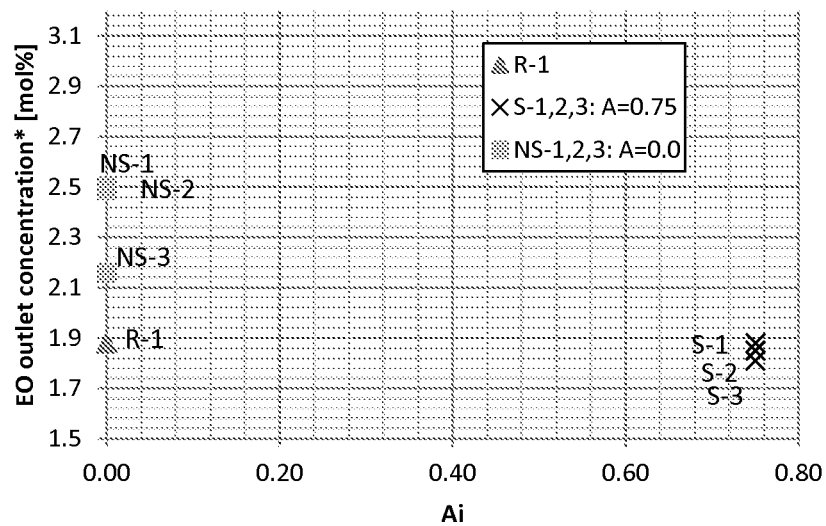
FIG. 1B is a graph of the corresponding reactor outlet ethylene oxide concentration at maximized efficiency versus a promoter scaling multiplier for the catalysts and process of FIG. 1A.
Figure 1C:
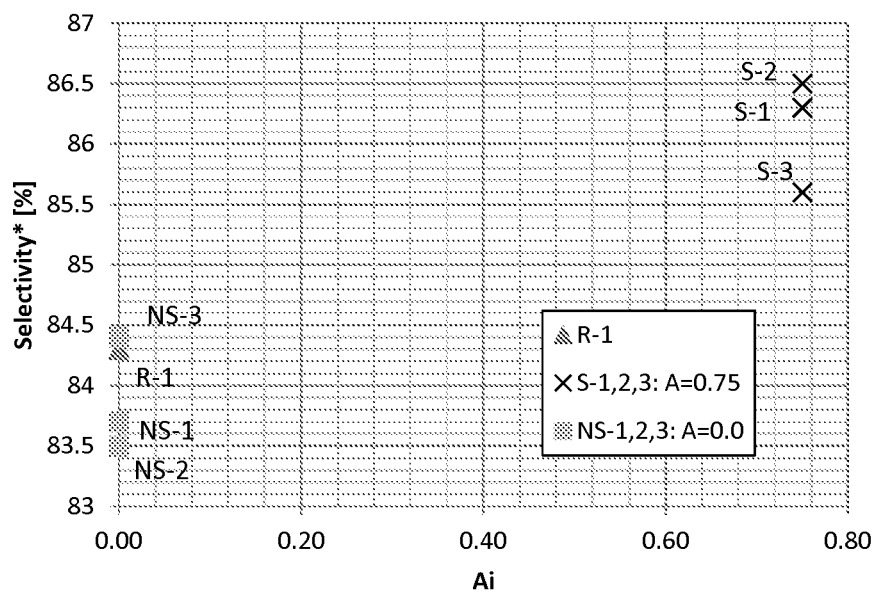
FIG. 1C is a graph of the maximized efficiency toward the production of ethylene oxide versus a promoter scaling multiplier for the catalysts and process of FIG. 1A.

FIG. 1(a) depicts the maximized efficiency toward ethylene oxide (selectivity) versus the corresponding reactor outlet ethylene oxide concentration for each of the catalysts and the reference catalyst R-1 at a reaction temperature of 231° C. FIG. 1(b) depicts the corresponding reactor outlet ethylene oxide concentration versus the promoter scaling multiplier $A_i$ for each of the catalysts. FIG. 1(c) depicts maximized efficiency versus the promoter scaling multiplier $A_i$ for each of the catalysts.

As FIGS. 1(a) to 1(c) indicate, those catalysts having a scaling multiplier of 0.75 show comparable corresponding values for reactor outlet ethylene oxide concentration relative to the reference catalyst R-1 and superior maximized efficiency values relative to the reference catalyst R-1. In contrast, the non-scaled catalysts ($A_i$=0) NS-1 to NS-3 have significantly higher corresponding reactor outlet ethylene oxide concentrations, with both NS-1 and NS-2 also achieving poorer maximized efficiency values than R-1.

Figure 2A:
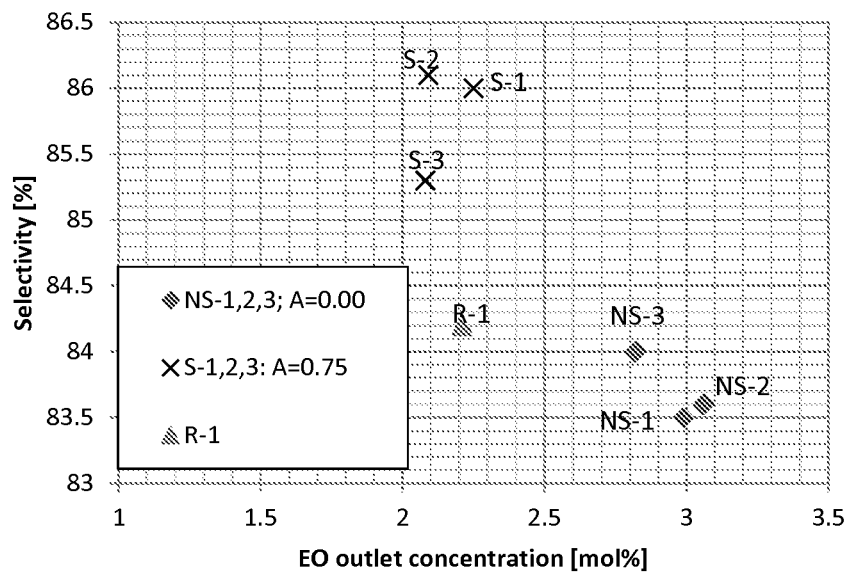
FIG. 2A is a graph of the maximized efficiency toward the production of ethylene oxide versus the corresponding reactor outlet ethylene oxide concentration in a process for making ethylene oxide from ethylene and oxygen using a variety of high-efficiency ethylene oxide catalysts with different promoter scaling multipliers at a reaction temperature of 236° C.
Figure 2B:
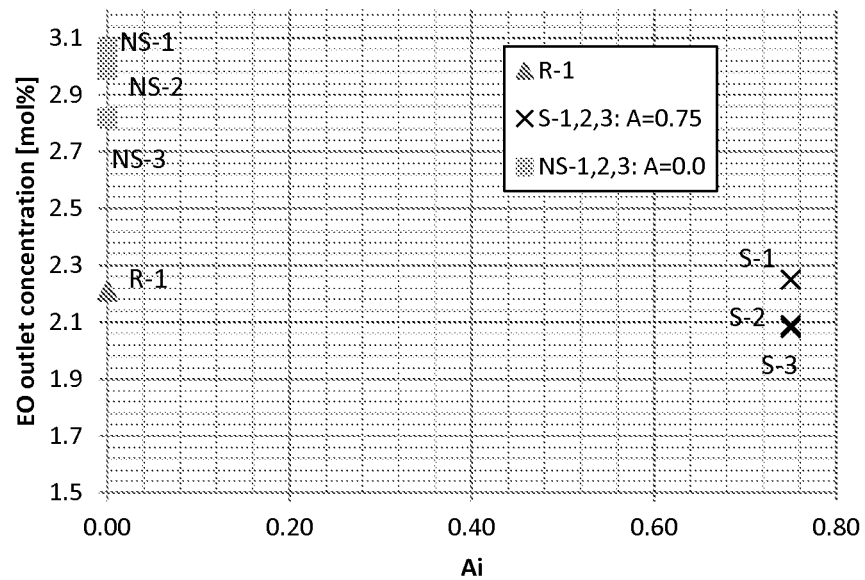
FIG. 2B is a graph of the corresponding reactor outlet ethylene oxide concentration at maximized efficiency versus a promoter scaling multiplier for the catalysts and process of FIG. 2A.
Figure 2C:
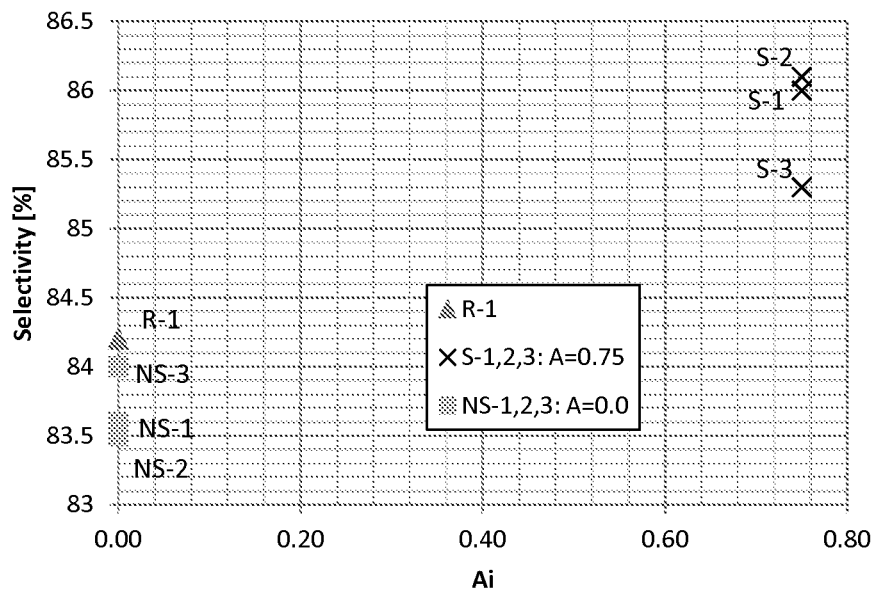
FIG. 2C is a graph of the maximized efficiency toward the production of ethylene oxide versus a promoter scaling multiplier for the catalysts and process of FIG. 2A.

FIG. 2(a) depicts maximized efficiency toward ethylene oxide (selectivity) at a reaction temperature of 236° C. versus the corresponding reactor outlet ethylene oxide concentration for the same catalysts. FIG. 2(b) depicts the corresponding reactor outlet ethylene oxide concentration versus the promoter scaling multiplier $A_i$ for each of the catalysts. FIG. 2(c) depicts maximized efficiency values versus the promoter scaling multiplier $A_i$ for each of the catalysts. Again, the promoter-scaled catalysts S-1 to S-3 show corresponding reactor outlet ethylene oxide values that are comparable to that of the reference catalyst R-1 while achieving superior maximized efficiencies relative to R-1. In contrast, the catalysts that are not promoter scaled (NS-1 to NS-3) exhibit significantly higher corresponding reactor outlet ethylene oxide concentration values relative to R-1 and poorer maximized efficiencies relative to R-1.

Averaged efficiency and ethylene oxide outlet concentration data for the two reaction temperatures are provided in Table 6 below:

TABLE 6

| Catalyst | Reaction Temperature of 231° C. | | Reaction Temperature of 236° C. | |
|---|---|---|---|---|
| | Ethylene Oxide Outlet Concentration (vol %) | Efficiency | Ethylene Oxide Outlet Concentration (vol %) | Efficiency |
| R-1 | 1.88 | 84.3 | 2.21 | 84.2 |
| S-1 | 1.88 | 86.3 | 2.25 | 86 |
| S-2 | 1.85 | 86.5 | 2.09 | 86.1 |
| S-3 | 1.81 | 85.6 | 2.08 | 85.3 |
| NS-1 | 2.49 | 83.7 | 2.99 | 83.5 |
| NS-2 | 2.5 | 83.5 | 3.06 | 83.6 |
| NS-3 | 2.16 | 84.4 | 2.82 | 84 |

The promoter-scaled S-1 to S-3 catalysts show an average maximized efficiency that is higher than that of the non-scaled NS-1 to NS-3 catalysts.

Example 4

The concentrations of scaled promoters used in the high-efficiency alkylene oxide catalysts of Examples 1-3 are calculated by using equation (1) (above) with carrier specific surface area as the reference property. In this example, the "power law" formula of equation (3) is used to calculate the concentrations. The catalysts are synthesized using a sequential vacuum impregnation method in which the carrier is dipped twice in a silver amine oxalate impregnation solution (without promoters) followed by a dip in a promoter impregnation solution (without silver).

In Table 7, below, carriers C-5 and C-6 are porous alpha-alumina carriers of the fluoride-mineralized, platelet-containing type. The carriers are double dipped in a silver oxalate impregnation solution and roasted as follows: About 50 g of the carrier pellets are loaded into a vacuum flask, sealed on the top by a Teflon stopper containing a vertical through hole. The glass drain tube of a separation funnel is inserted into the vertical hole and held in place by a compression fitting with a rubber o-ring to ensure a good seal. The flask is evacuated at 70 mm Hg for 15 minutes by a mechanical pump connected through a trap submerged in ice water. The silver oxalate solution is poured into the separation funnel, the vacuum line to the vacuum flask is closed, and the stopcock on the separation funnel is opened, covering the evacuated alumina carrier pellets with the silver oxalate impregnation solution. The vacuum is then broken to atmosphere and the pellets are allowed to soak for 15 minutes. After soaking, the bottom stopcock of the vacuum flask is opened, allowing excess silver oxalate impregnation solution to drain from the catalyst pellets. Wet catalyst pellets are placed in a pre-heated muffle furnace and roasted at 500° C. for 5 minutes. The vacuum impregnation and roasting procedures are repeated a second time to obtain the desired silver loading.

Silver loadings on the two carriers are determined following the second silver dip using a titration method:

TABLE 7

| Carrier | Specific surface area (m²/g) | Pore volume (cm³/g) | Silver loading (wt. %) |
|---|---|---|---|
| C-5 | 1.05 | 0.68 | 34.6 |
| C-6 | 1.29 | 0.70 | 34.5 |

In this example, six promoters (Cs, Na, Li, Re, sulfate, and Mn) are scaled promoters. Each promoter has a respective "second" catalyst target concentration value that is determined based on the power law equation (equation (3)).

The promoter loading process is as follows: Pellets of the silver loaded C-5 and C-6 carriers are ground and sieved to 30/50 standard U.S. mesh. Diluted precursor solutions of cesium hydroxide, lithium acetate, sodium acetate, ammonium sulfate, ammonium perrhenate, and a solution comprising manganese (II) nitrate are prepared separately. Using an impregnation station, the precursor solutions are impregnated on the crushed, silver-loaded carrier pellets using incipient wetness methodology and an incipient wetness factor of 0.350-0.367. After impregnation, the samples are dried over night in a fume hood and then roasted at 550° C. for 10 minutes in a muffle furnace. Using this procedure, reference catalyst R-4 is prepared on carrier C-5 (1.05 m²/g) with the promoter concentrations as given in Table 9.

Several other catalysts are prepared in the foregoing manner using carrier C-6 (1.29 m²/g). Values of the scaling multiplier ($A_i$) and scaling exponent ($\alpha i$) are calculated for each catalyst and are the same amongst all promoters on each catalyst. The properties of the catalysts are set forth in Tables 8 and 9 below:

TABLE 8

| Catalyst | Specific surface Area (m2/g) | Pore volume (cm3/g) | $SA_{cat}/SA_{R-4}$ | $A_i$ | $\alpha i$ |
|---|---|---|---|---|---|
| R-4 | 1.05 | 0.68 | — | — | — |
| VS-6 | 1.29 | 0.7 | 1.23 | -1.31 | -1.73 |
| VS-7 | 1.29 | 0.7 | 1.23 | -0.66 | -0.79 |
| NS-6 | 1.29 | 0.7 | 1.23 | 0 | 0 |
| NS-7 | 1.29 | 0.7 | 1.23 | 0 | 0 |
| NS-8 | 1.29 | 0.7 | 1.23 | 0 | 0 |
| S-4 | 1.29 | 0.7 | 1.23 | 0.66 | 0.68 |
| S-5 | 1.29 | 0.7 | 1.23 | 1.31 | 1.27 |

TABLE 9

| Catalyst | Cs (ppm) | Li (ppm) | Na (ppm) | $[SO_4]^{-1}$ (ppm) | Re (ppm) | Mn (ppm) |
|---|---|---|---|---|---|---|
| R-4 | 585 | 29 | 37 | 139 | 391 | 115 |
| VS-6 | 385 | 20 | 25 | 99 | 279 | 82 |
| VS-7 | 478 | 25 | 32 | 119 | 335 | 99 |
| NS-6 | 558 | 29 | 37 | 139 | 391 | 115 |
| NS-7 | 558 | 29 | 37 | 139 | 391 | 115 |
| NS-8 | 558 | 29 | 37 | 139 | 391 | 115 |
| S-4 | 638 | 33 | 42 | 159 | 447 | 131 |
| S-5 | 731 | 38 | 49 | 179 | 503 | 148 |

Figure 3A:
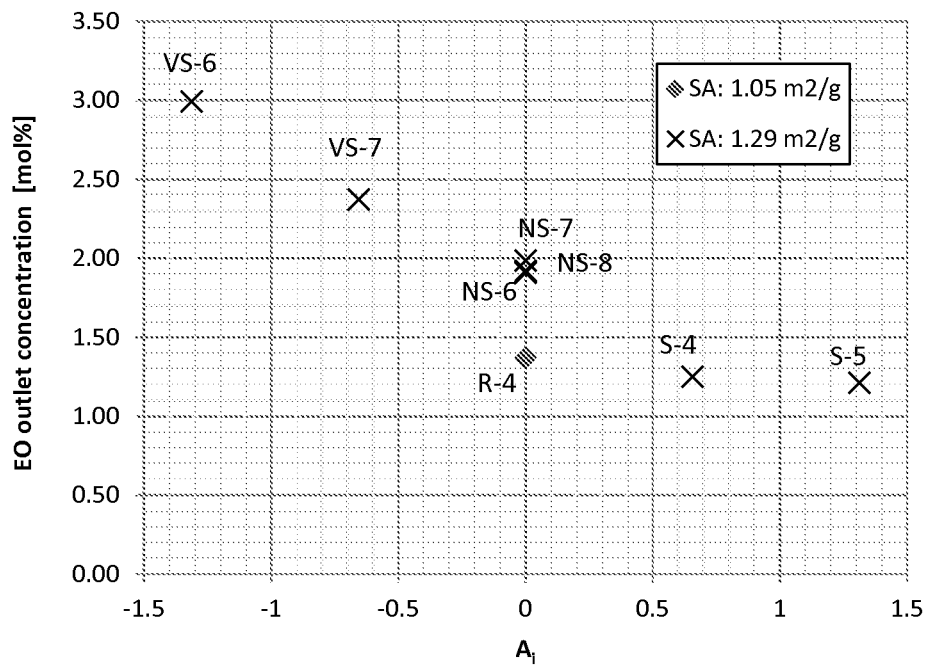
FIG. 3A is a graph of the corresponding reactor outlet ethylene oxide concentration at maximized efficiency versus a promoter scaling multiplier in a process for making ethylene oxide from ethylene and oxygen using a variety of high-efficiency ethylene oxide catalysts with different promoter scaling multipliers at a reaction temperature of 236° C.
Figure 3B:
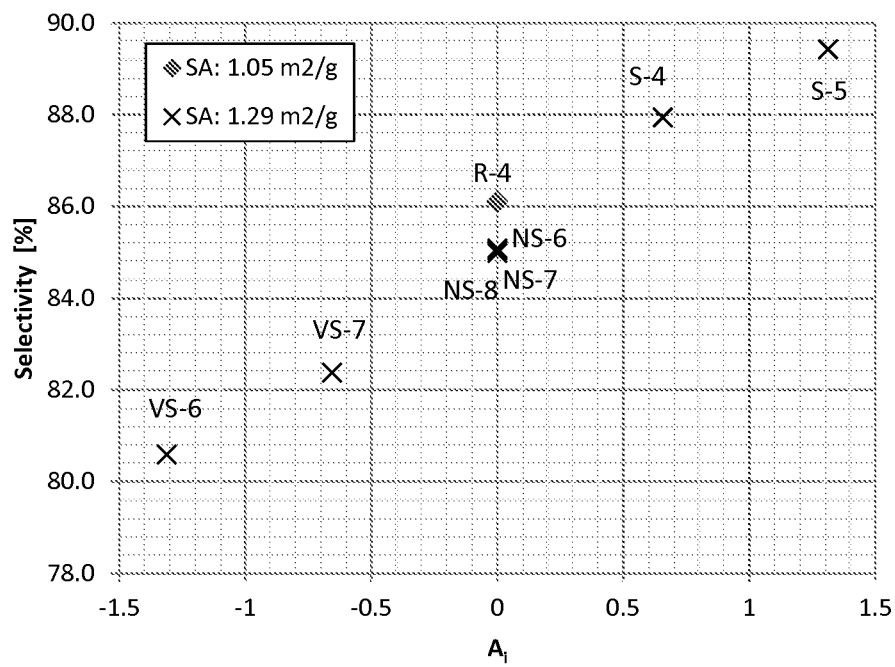
FIG. 3B is a graph of the maximized efficiency toward the production of ethylene oxide versus a scaling multiplier for the process and catalysts of FIG. 3A.
Figure 4A:
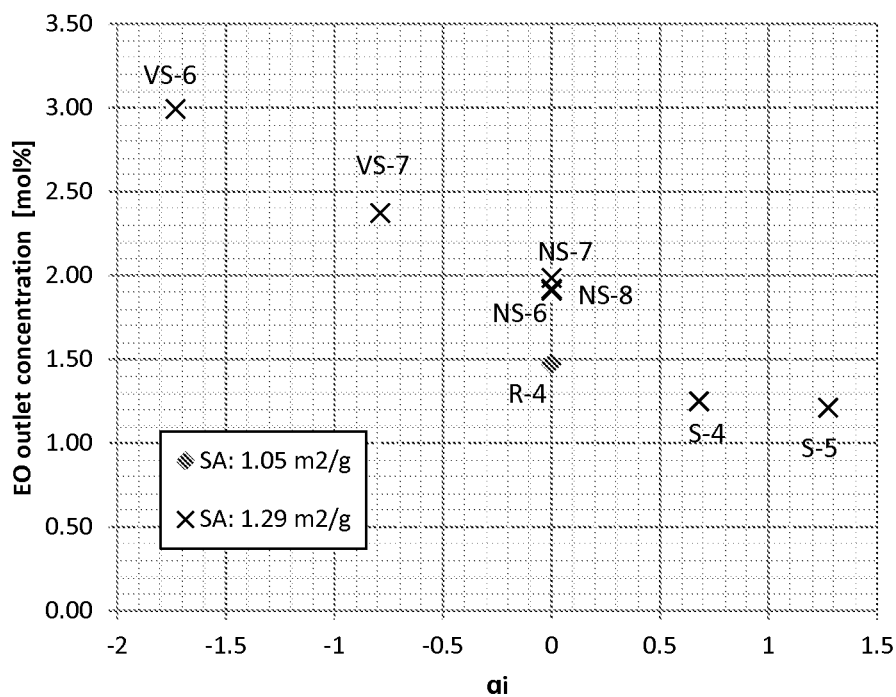
FIG. 4A is a graph of the corresponding reactor outlet ethylene oxide concentration at maximized efficiency versus a promoter scaling exponent for the catalysts and process of FIG. 3A.
Figure 4B:
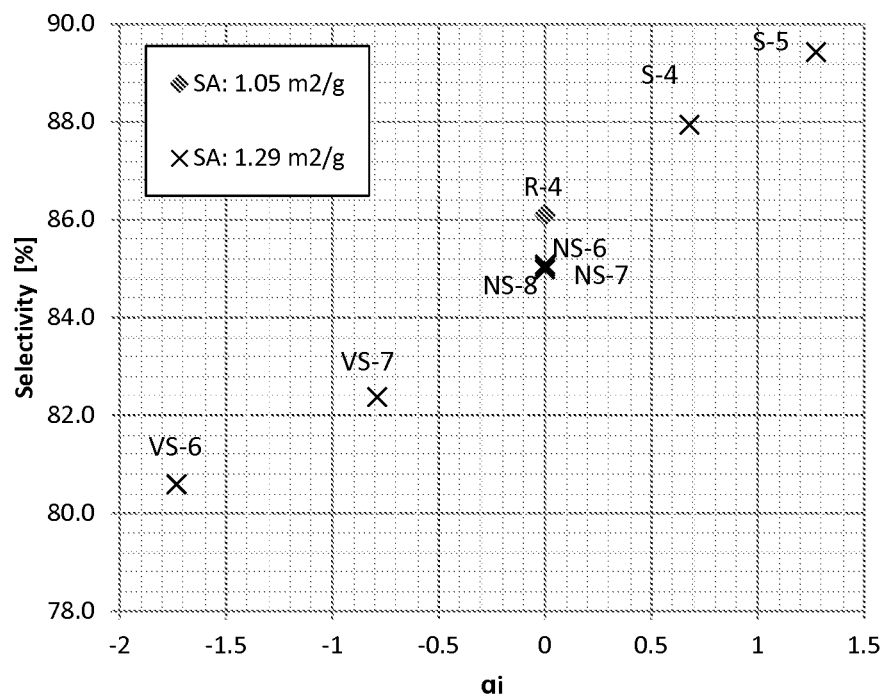
FIG. 4B is graph of the maximized efficiency toward the production of ethylene oxide versus a promoter scaling exponent for the catalysts and process of FIG. 3A.

The catalysts are then subjected to an epoxidation feed gas in an HPRAM reactor at 236° C. in the manner described above with respect to FIGS. 1(a)-1(c). Efficiency-maximizing Z*, the corresponding reactor outlet ethylene oxide concentrations, and maximized efficiencies toward ethylene oxide are calculated in the manner described above with respect to FIGS. 1(a)-1(c). FIG. 3(a) depicts the corresponding reactor outlet ethylene oxide concentrations versus the scaling multiplier $A_i$ for each of the catalysts. FIG. 3(b) depicts the maximized efficiency towards ethylene oxide versus the scaling multiplier $A_i$ for each of the catalysts. FIGS. 4(a) and 4(b) are analogous to FIGS. 3(a) and 3(b) except that the power law scaling exponent $\alpha i$ is plotted on the x-axis.

FIGS. 3(a)/(b) and 4(a)/(b) each indicate that catalysts S-4 and S-5 achieve corresponding reactor outlet ethylene oxide concentrations comparable to those of reference catalyst R-4 while achieving significantly better maximized efficiency than R-4. In contrast, the VS-6 and VS-7 catalysts and the non-promoter scaled NS-6 to NS-8 catalysts have higher corresponding reactor outlet ethylene oxide concentrations and poorer maximized efficiency than R-4. As indicated in FIGS. 3(a)/(b) and 4(a)/(b), the VS-6 and VS-7 catalysts with negative scaling multiplier $A_i$ values and negative scaling exponent $\alpha i$ values achieve higher corresponding reactor outlet ethylene oxide concentrations and poorer maximized efficiencies than R-4. Thus, the best results are obtained with an $A_i$ value of 0.66 or 1.31 and an $\alpha i$ value of 0.68 and 1.27.

What is claimed is:

1. A method for making a second high efficiency, alkylene oxide catalyst based on the properties of a first high efficiency alkylene oxide catalyst, wherein the first high efficiency alkylene oxide catalyst comprises a carrier, silver, a promoting amount of at least one promoter, the at least one promoter comprising a rhenium promoter, the method comprising:
   determining a respective target concentration value on the second catalyst for one or more of the at least one promoter based on values of a catalyst reference property for the first and second catalysts and a respective concentration value of the one or more of the at least one promoter on the first catalyst, wherein the step of determining the respective target concentration value on the second catalyst for one or more of the at least one promoter comprises determining the respective target concentration value in accordance with a monotonic relationship between the target concentration value and the catalyst reference property, and the monotonic relationship is not a linear proportional relationship; and
   preparing the second high efficiency catalyst based on the respective target concentration value on the second catalyst for the one or more of the at least one promoter.

2. The method of claim 1, wherein the catalyst reference property is carrier specific surface area.

3. The method of claim 1, wherein the catalyst reference property is silver specific surface area.

4. The method of claim 1, wherein the monotonic relationship is a linear relationship.

5. The method of claim 1, wherein the monotonic relationship is a spline consisting of two mathematical formulas, and the spline knot is placed at the catalyst reference property value of the first catalyst.

6. The method of claim 5, wherein a first one of the two mathematical formulas is represented as follows:

$$CP_{2i}=CP_{1i}(1+A_i(RP_2/RP_1-1))$$

wherein i is an index corresponding to a particular promoter, $CP_{1i}$ is the concentration value of the ith promoter on the first catalyst, $CP_{2i}$ is the target concentration value of the ith promoter on the second catalyst, RP$_2$ is the value of the catalyst reference property for the second catalyst, RP$_1$ is the value of the catalyst reference property for the first catalyst, and A$_i$ is a non-zero scaling multiplier for the ith promoter.

7. The method of claim 6, wherein a second one of the two mathematical formulas is represented as follows:

$$CP_{2i}=CP_{1i}/(1+A_i(RP_1/RP_2-1))$$

wherein i is an index corresponding to a particular promoter,

CP$_{1i}$ is the concentration value of the ith promoter on the first catalyst,

CP$_{2i}$ is the target concentration value of the ith promoter on the second catalyst, RP$_2$ is the value of the catalyst reference property for the second catalyst, RP$_1$ is the value of the catalyst reference property for the first catalyst, and A$_i$ is a non-zero scaling multiplier for the ith promoter.

8. The method of claim 7, wherein the catalyst reference property is the carrier specific surface area, the first one of the two mathematical formulas is used where RP$_2$/RP$_1 \geq 1$, and the second one of the mathematical formulas is used where RP$_2$/RP$_1 < 1$.

9. The method of claim 1, wherein the monotonic relationship is represented by the following formula:

$$CP_{2i}=CP_{1i}(RP_2/RP_1)^{\alpha i}$$

wherein i is an index corresponding to a particular promoter,

CP$_{1i}$ is the concentration value of the ith promoter on the first catalyst,

CP$_{2i}$ is the target concentration value of the ith promoter on the second catalyst, RP$_2$ is the value of the reference property for the second catalyst, RP$_1$ is the value of the reference property for the first catalyst, and αi is a non-zero scaling exponent for the ith promoter.

10. A method for making a second high-efficiency alkylene oxide catalyst in accordance with claim 1, wherein the one or more of the at least one promoter comprises at least one of at least one alkali metal, the rhenium promoter, and a rhenium co-promoter.

* * * * *